US008401801B2

(12) United States Patent
Mrazek et al.

(10) Patent No.: US 8,401,801 B2
(45) Date of Patent: Mar. 19, 2013

(54) METHODS FOR SELECTING MEDICATIONS

(75) Inventors: David A. Mrazek, Rochester, MN (US);
Dennis J. O'Kane, Rochester, MN (US);
John L. Black, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1136 days.

(21) Appl. No.: 10/545,931

(22) PCT Filed: Feb. 20, 2004

(86) PCT No.: PCT/US2004/005113
§ 371 (c)(1),
(2), (4) Date: Jun. 23, 2006

(87) PCT Pub. No.: WO2004/074456
PCT Pub. Date: Sep. 2, 2004

(65) Prior Publication Data
US 2007/0003931 A1    Jan. 4, 2007

Related U.S. Application Data

(60) Provisional application No. 60/448,547, filed on Feb. 20, 2003.

(51) Int. Cl.
*G06F 19/10* (2011.01)
*G06F 19/18* (2011.01)
(52) U.S. Cl. .......................................... 702/20; 435/6.11
(58) Field of Classification Search ........................ None
See application file for complete search history.

(56) References Cited

U.S. PATENT DOCUMENTS

| 5,451,683 | A | 9/1995 | Barrett et al. | |
| 6,081,786 | A * | 6/2000 | Barry et al. | 705/3 |
| 6,183,963 | B1 | 2/2001 | Sinnett et al. | |
| 6,297,014 | B1 * | 10/2001 | Taylor et al. | 435/6 |
| 6,812,339 | B1 * | 11/2004 | Venter et al. | 435/6 |
| 2001/0034023 | A1 * | 10/2001 | Stanton et al. | 435/6 |
| 2002/0010552 | A1 * | 1/2002 | Rienhoff et al. | 705/3 |
| 2002/0010595 | A1 | 1/2002 | Kapp | |
| 2002/0076774 | A1 | 6/2002 | Yan et al. | |
| 2002/0091664 | A1 | 7/2002 | Larder et al. | |
| 2002/0187483 | A1 * | 12/2002 | Hoffman et al. | 435/6 |
| 2003/0046110 | A1 | 3/2003 | Gogolak | |
| 2003/0046114 | A1 * | 3/2003 | Davies et al. | 705/3 |
| 2003/0104453 | A1 * | 6/2003 | Pickar et al. | 435/6 |
| 2003/0157110 | A1 | 8/2003 | An et al. | |
| 2003/0169763 | A1 | 9/2003 | Choi et al. | |
| 2003/0170176 | A1 | 9/2003 | Leyland-Jones | |
| 2003/0204415 | A1 * | 10/2003 | Knowlton | 705/2 |
| 2004/0260666 | A1 | 12/2004 | Pestotnik et al. | |
| 2006/0289019 | A1 | 12/2006 | Marchand et al. | |

FOREIGN PATENT DOCUMENTS

| JP | 2002024385 A | 1/2002 |
| JP | 2002197189 A | 7/2002 |
| JP | 2002245171 A | 8/2002 |
| WO | WO 98/20019 | 5/1998 |
| WO | WO 00/50639 | 8/2000 |
| WO | WO-0212434 A2 | 2/2002 |
| WO | WO-03008637 A2 | 10/2003 |
| WO | WO 2004/074456 | 9/2004 |
| WO | WO-2005038049 A2 | 4/2005 |
| WO | WO-2005109238 A2 | 11/2005 |
| WO | WO 2006/075254 | 7/2006 |
| WO | WO-2007064675 A2 | 6/2007 |

OTHER PUBLICATIONS

Johnson, J. A. et al. Pharmacogenomics: A scientific revolution in pharmaceutical sciences and pharmacy practice. report of the 2001-2002 academic affairs committee. American Journal of Pharmaceutical Education 66, 12S-15S (2002).*
Klein, T. E. et al. Integrating genotype and phenotype information: an overview of the pharmgkb project. The pharmacogenomics journal 1, 167-170 (2001).*
Catalano, M. Functionally gene-linked polymorphic regions and genetically controlled neurotransmitters metabolism. European Neuropsychopharmacology 11, 431-439 (2001).*
Kim, D. K. et al. Serotonin transporter gene polymorphism and antidepressant response. NeuroReport 11, 215-219 (2000).*
Lachman, H. M. et al. Human catechol-O-methyltransferase pharmacogenetics: description of a functional polymorphism and its potential application to neuropsychiatric disorders. Pharmacogenetics 6, 243-250 (1996).*
Minov, C. et al. Serotonin-2A-receptor and -transporter polymorphisms: lack of association in patients with major depression. Neuroscience Letters 303, 119-122 (2001).*
Serretti, A. et al. Influence of tryptophan hydroxylase and serotonin transporter genes on fluvoxamine antidepressant activity. Molecular Psychiatry 6, 586-592 (2001).*
Tanaka, E. & Hisawa, S. Clinically significant pharmacokinetic drug interactions with psychoactive drugs: antidepressants and antipsychotics and the cytochrome p450 system. Journal of Clinical Pharmacy and Therapeutics 24, 7-16 (1999).*
Arranz et al., "Pharmacogenetics for the individualization of psychiatric treatment," *Am. J.Pharmacogenomics*, 2001, 1:3-10.
Bishop and Ellingrod, "Neuropsychiatric pharmacogenetics: moving toward a comprehensive understanding of predicting risks and response," *Pharmacogenomics*, 2004, 5(5):463-477.
Bondy and Zill, "Pharmacogenetics and psychopharmacology," *Curr. Opin. Pharmacol.*, 2004, 4:72-78. Coutts and Urichuk, "Polymorphic cytochromes P450 and drugs used in psychiatry," *Cell. Mol. Neurobiol.*, 1999, 19(3):325-354.
Kerwin et al., "Genetic strategies for the personalization of antipsychotic treatment," *Exp. Rev. Mol. Diagnostics, Future Drugs*, 2001, 1:275-280.
Mitchell, "Therapeutic drug monitoring of psychotrophic medications," *Bri. J. Clin. Pharmacol.*, 2000, 49(4):303-312.

(Continued)

*Primary Examiner* — Soren Harward
(74) *Attorney, Agent, or Firm* — Muriel Liberto; Ivor Elrifi; Mintz Levin Cohn Ferris Glovsky and Popeo, P.C.

(57) ABSTRACT

Methods for selecting a medication for a patient are described that include determining the patient's genotype for a panel of genes and selecting the medication based on the genotype. Articles of manufacture also are provided that include nucleic acid molecules for detecting alleles of genes encoding drug metabolizing enzymes and genes encoding products involved in neurotransmission.

10 Claims, 2 Drawing Sheets

OTHER PUBLICATIONS

Serretti et al., "Pharmacogenetics in affective disorders," *Eur. J. Pharmacol.*, 2002, 438:117-128.
Kawanishi et al., "Pharmacogenetics and schizophrenia," *Eur. J. Pharmacol.*, 2000, 410:227-241.
Devane, "Pharmacogenetics and drug metabolism of newer antidepressant agents," *J. Clin. Psychiatry*, 1994, 55:38-47.
Jain, "Application of Biochip and Microarray Systems in Pharmacogenomics," *Pharmacogenomics*, 2000, 1:289-307.
Variagenics: "Gene sequence variations with utility in determining the treatment of disease," EPODOC, 2000.
Hewett et al., "PharmGKB: the Pharmacogenetics Knowledge Bas," *Nucl. Acids Res.*, 2002, 30:163-165.
Brockmöller et al., "Pharmacogenetic diagnostics of cytochrome P450 polymorphisms in clinical drug development and in drug treatment," *Pharmacogenomics*, 2000, 1(2):125-151.
Comings et al., "The additive effect of neurotransmitter genes in pathological gambling," *Clin Genet.*, 2001, 60:107-116.
Comings et al., "Comparison of the role of dopamine, serotonin, and noradrenaline genes in ADHD, ODD and conduct disorder; multivariate regression analysis of 20 genes," *Clin. Genet.*, 2000, 57: 178-196.
Comings et al., "Multivariate analysis of associations of 42 genes in ADHD, ODD and conduct disorder," *Clin. Genet.*, 2000, 58:31-40.
Dalma-Weiszhausz and Murphy, Jr., "Single nucleotide polymorphisms and their characterization with oligonucleotide microarrays," *Psychiatric Genetics*, 2002, 12(2):97-107.
Drmanac et al., "DNA Sequence Determination by Hybridization: A Strategy for Efficient Large-Scale Sequencing," *Science*, 1993, 260:1649-1652.
Guatelli et al., "Isothermal, in vitro amplification of nucleic acids by a multienzyme reaction modeled after retroviral replication," *Proc. Natl. Acad. Sci. USA*, 1990, 87:1874-1878.
Ibeanu et al., "A Novel Transversion in the Intron 5 Donor Splice Junction of *CYP2C19* and a Sequence Polymorphism in Exon 3 Contribute to the Poor Metabolizer Phenotype for the Anticonvulsant Drug S-Mephenytoin," *J. Pharmacol. Exp. Ther.*, 1999, 290(2):635-640.
Kirchheiner et al., "CYP2D6 and CYP2C19 genotype-based dose recommendations antidepressants: a first step towards subpopulation-specific dosages," *Acta Psychiatr. Scand.*, 2001, 104:173-192.
Lewis, "PCR's Competitors Are Alive and Well and Moving Rapidly Towards Commercialization," *Genetic Engineering News*, 1992, 12(9):1, 3 pages.
Myakishev et al., "High-Throughput SNP Genotyping by Allele-Specific PCR with Universal Energy-Transfer-Labeled Primers," *Genome Research*, 2001, 11:163-169.
Prince et al., "Robust and Accurate Single Nucleotide Polymorphism Genotyping by Dynamic Allele-Specific Hybridization (DASH): Design Criteria and Assay Validation," 11(1):152-162 *Genome Res.*, 2001, 11(1): 152-162.
Sachse et al., "Functional significance of a C→ A polymorphism in intron I of the cytochrome P450 *CYP1A2* gene tested with caffeine," *Br. J. Clin. Pharmacol.*, 1999, 47:445-449.
Sallee et al., "Fluoxetine-Related Death in a Child with Cytochrome P-450 2D6 Genetic Deficiency," *J. Child Adol. Psychopharmacol*, 2000, 10(1):27-34.
Steimer and Potter, "Pharmacogenetic screening and therapeutic drugs," *Clin. Chim. Acta*, 2002, 315:137-155.
Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.
Weiss, "Hot Prospect for New Gene Amplifier," *Science*, 1991, 254:1292-1293.
Wong et al., "Pharmacogenetics: the Molecular Genetics of *CYP2D6* Dependent Drug Metabolism," *Am. Acad. Med. Singapore*, 2000, 29:401-406.
European Patent Office, Office Action issued Feb. 10, 2009, EP Application No. 04-713-4044.4-2402.
European Patent Office, Office Action issued Jul. 2, 2010, EP Application No. 04-713-4044.4-2402.
Japanese Patent Office, Office Action issued Nov. 8, 2010, JP Application No. 2006-503753.
Office Action in EP 07 84 0663 mailed Jul. 5, 2010, 5 pages.
Supplementary European Search Report in EP 07 84 0663 mailed Jan. 4, 2010, 7 pages.
Kirchheiner "Pharmacogenetics in Psychiatry—A Useful Clinical Tool or Wishful thinking for the Future?" Current Pharmaceutical Design, 2010, 16, 136-144.
Kirchheiner et al., "Pharmacogenetics of antidepressants and antipsychotics: the contribution of allelic variations to the phenotype of drug response," *Mol. Psychiatry*, 2004, 9:442-473.
Ueda et al., "The Impact of CYP2D6 genotypes on the plasma concentration of paroxetine in Japanese psychiatric patients," Progress in Neuro-Phychopharmacology & Biological Psychiatry 30 (2006) 486-491.
McMahon et al. "Variation in the Gene Encoding the Serotonin 2A Receptor is Associated with Outcome of Antidepressant Treatment", Am. J. Human. Gene., 78:804-814 (2006).
Black et al., "The impact of CYP allelic variation on antidepressant metabolism: a review", Exp. Opin. Drug Metab. Toxicol., 3(1):21-31 (2007).
Kung et al., "The Clinical Use of Pharmacogenomic Testing in Treatment-Resistant Depression", Prim. Psych., 17(5):46-51 (2010).
Wall et al., "Safety and Efficacy Pharmacogenomics in Pediatric Psychopharmacology", Prim. Pysch., 17(5):53-58 (2010).
Hall-Flavin et al. "Assessing the Clinical Impact of a Pharmacogenomic Algorithm in a Psychiatric Outpatient Clinical Setting", Submitted Manuscript 2011.
Evans, et al. "Pharmacogenomics: Translating Functional Genomics into Rational Therapeutics." Science. 286.5439(1999):487-491.
Cusin et al. "Influence of Monoamine Oxidase A and Serotonin Receptor 2A Polymorphisms in SSRI Antidepressant Activity." *Int. J. Neuropsychopharmacol.* 5.1(2002):27-35.
Lotrich et al. "Polymorphism of the Serotonin Transporter: Implications for the Use of the Selective Serotonin Reuptake Inhibitors." *Practical Pharmacogenomics.* 1.3(2001):153-164.
Steimer et al. "Pharmacogenetics: A New Diagnostic Tool in the Management of Antidepressive Drug Therapy." *Clin. Chim. Acta.* 308.1-2(2001):33-41.
Chou et al. "Comparison of Two *CYP2D6* Genotyping Methods and Assessment of Genotype-Phenotype Relationships." *Clin. Chem.* 49.4(2003):542-551.
Raimundo et al. "A Novel Intronic Mutation, 2988G>A, With High Predictivity for Impaired Function of Cytochrome P450 2D6 in White Subjects." *Clin. Pharmacol. Ther.* 76.2(2004):128-138.
Luo et al. "Identification of *CYP2D6* Impaired Functional Alleles in Mexican Americans." *Eur. J. Clin. Pharmacol.* 61.11(2005):797-802.
McAlpine et al. "Cytochrome P450 *2D6* Genotype Variation and Venlafaxine Dosage." *Mayo Clin. Proc.* 82.9(2007):1065-1068.
Rasmussen et al. "CYP2D6 Gene Test in Psychiatric Patients and Healthy Volunteers." *Scand. J. Clin. Lab. Inv.* 66.2(2006):129-136.
Ereshefsky et al. "Review of the Phermacokinetics, Pharmacogenetics, and Drug Interaction Potential of Antidepressants: Focue on Venlafaxine." *Depress. Anxiety.* 12.S1(2000):30-44.
Griese et al. "Assessment of the Predictive Power of Genotypes for the in-vivo Catalytic Function of CYP2D6 in a German Population." *Pharmacogenetics.* 8.1(1998):15-26.
Ingelman-Sundberg et al. "Polymorphic Human Cytochrome P450 Enzymes: An Opportunity for Individualized Drug Treatment." *Trends Pharmacol. Sci.* 20.8(1999):342-349.
Kirchheiner et al. "Pharmacogenetics-Based Therapeutic Recommendations—Ready for Clinical Practice?" *Nat.Rev. Drug Disc.* 4.8(2005):639-647.
McElroy et al. "CYP2D6 Genotyping as an Alternative to Phenotyping for Determination of Metabolic Status in a Clinical Trial Setting." *AAPS Pharmsci.* 2.4(2000):1-11.
Meisel et al. "How to Manage Individualized Drug Therapy: Application of Pharmacogenetic Knowledge of Drug Metabolism and Transport." *Clin. Chem. Lab. Med.* 38.9(2000):869-876.
Hung et al. "Dosage Recommendation of Phenytoin for Patients with Epilepsy with Different CYP2C9/CYP2C19 Polymorphisms." *Ther. Drug Monit.* 26.5(2004):534-540.

\* cited by examiner

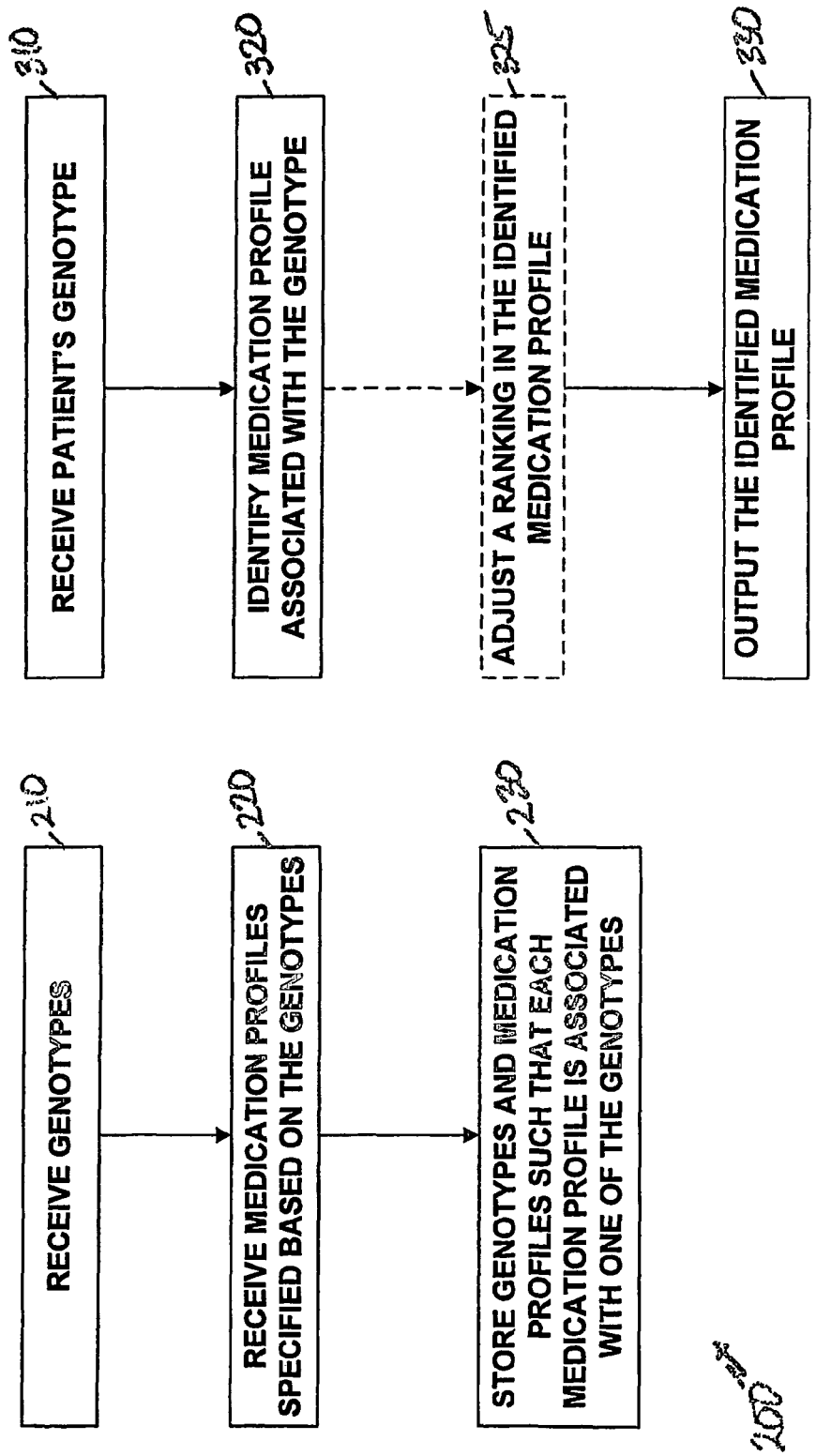

SEQUENCE LISTING

```
<160> NUMBER OF SEQ ID NOS: 180

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
ccagaaggct ttgcaggctt ca                                            22

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
actgagccct gggaggtagg ta                                            22

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide

<400> SEQUENCE: 3
ggcctaccct gggtaagggc ctggagcagg a                                  31

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide

<400> SEQUENCE: 4
cctggtcgaa gcagtat                                                  17

<210> SEQ ID NO 5
<211> LENGTH: 10
<212> TYPE: DNA
<213> ORGANISM: Artificial Sequence
<220> FEATURE:
<223> OTHER INFORMATION: Oligonucleotide

<400> SEQUENCE: 5
```
gcacgctacc                                                          10

<210> SEQ ID NO 6
<211> LENGTH: 10
<212> TYPE: DNA
<213> ORGANISM: Artificial Sequence
<220> FEATURE:
<223> OTHER INFORMATION: Oligonucleotide

<400> SEQUENCE: 6
gcacgctact                                                          10

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
caccaggccc cctgccactg                                               20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
cctgctcact cctggtagcc                                               20

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide

<400> SEQUENCE: 9
ctgtttcatg tccacgacc                                                19

<210> SEQ ID NO 10
<211> LENGTH: 10
<212> TYPE: DNA
<213> ORGANISM: Artificial Sequence
<220> FEATURE:
<223> OTHER INFORMATION: Oligonucleotide

<400> SEQUENCE: 10
tgcccatcac                                                          10

<210> SEQ ID NO 11
<211> LENGTH: 10
<212> TYPE: DNA
<213> ORGANISM: Artificial Sequence
<220> FEATURE:
<223> OTHER INFORMATION: Oligonucleotide

<400> SEQUENCE: 11
tgcccatcat                                                          10

<210> SEQ ID NO 12
<211> LENGTH: 24
<212> TYPE: DNA
<213> ORGANISM: Artificial Sequence
<220> FEATURE:

<223> OTHER INFORMATION: Oligonucleotide

<400> SEQUENCE: 12
ccagatcctg ggtttcgggc cgcg                                              24

<210> SEQ ID NO 13
<211> LENGTH: 16
<212> TYPE: DNA
<213> ORGANISM: Artificial Sequence
<220> FEATURE:
<223> OTHER INFORMATION: Oligonucleotide

<400> SEQUENCE: 13
cagaggcgct tctccg                                                       16

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
ctcggtctct cgctccgcac                                                   20

<210> SEQ ID NO 15
<211> LENGTH: 10
<212> TYPE: DNA
<213> ORGANISM: Artificial Sequence
<220> FEATURE:
<223> OTHER INFORMATION: Oligonucleotide

<400> SEQUENCE: 15
cttctccgtg                                                              10

<210> SEQ ID NO 16
<211> LENGTH: 10
<212> TYPE: DNA
<213> ORGANISM: Artificial Sequence
<220> FEATURE:
<223> OTHER INFORMATION: Oligonucleotide

<400> SEQUENCE: 16
cttctccgtc                                                              10

<210> SEQ ID NO 17
<211> LENGTH: 26
<212> TYPE: DNA
<213> ORGANISM: Artificial Sequence
<220> FEATURE:
<223> OTHER INFORMATION: Oligonucleotide

<400> SEQUENCE: 17
tccaccttgc gcaacttggg cctggg                                            26

<210> SEQ ID NO 18
<211> LENGTH: 10
<212> TYPE: DNA
<213> ORGANISM: Artificial Sequence
<220> FEATURE:
<223> OTHER INFORMATION: Oligonucleotide

<400> SEQUENCE: 18
ccacccccag                                                              10

<210> SEQ ID NO 19

```
<211> LENGTH: 10
<212> TYPE: DNA
<213> ORGANISM: Artificial Sequence
<220> FEATURE:
<223> OTHER INFORMATION: Oligonucleotide

<400> SEQUENCE: 19
ccacccccaa                                                                 10

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide

<400> SEQUENCE: 20 gacgccccttt tcgccccaac g                                                   21

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
tgagacttgt ccaggtgaac                                                      20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide

<400> SEQUENCE: 22
cccagatggg ctcacgctgc                                                      20

<210> SEQ ID NO 23
<211> LENGTH: 10
<212> TYPE: DNA
<213> ORGANISM: Artifiical Sequence

<400> SEQUENCE: 23
actgagcaca                                                                 10

<210> SEQ ID NO 24
<211> LENGTH: 10
<212> TYPE: DNA
<213> ORGANISM: Artificial Sequence
<220> FEATURE:
<223> OTHER INFORMATION: Oligonucleotide

<400> SEQUENCE: 24
actgagcacg                                                                 10

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide

<400> SEQUENCE: 25
ggatgacctg ggacccagcc cagcc                                                25
```

```
<210> SEQ ID NO 26
<211> LENGTH: 10
<212> TYPE: DNA
<213> ORGANISM: Artificial Sequence
<220> FEATURE:
<223> OTHER INFORMATION: Oligonucleotide

<400> SEQUENCE: 26
gagaacctgc                                                              10

<210> SEQ ID NO 27
<211> LENGTH: 10
<212> TYPE: DNA
<213> ORGANISM: Artificial Sequence
<220> FEATURE:
<223> OTHER INFORMATION: Oligonucleotide

<400> SEQUENCE: 27
gagaacctgt                                                              10

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide

<400> SEQUENCE: 28
gcatagtggt ggctgacctg ttctctg                                           27

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide

<400> SEQUENCE: 29
cccccgctga ctcccctctg                                                   20

<210> SEQ ID NO 30
<211> LENGTH: 21
<212> TYPE: DNA
<213> ORGANISM: Artificial Sequence
<220> FEATURE:
<223> OTHER INFORMATION: Oligonucleotide

<400> SEQUENCE: 30 gaccccgag cctcaccttc c                                                  21

<210> SEQ ID NO 31
<211> LENGTH: 10
<212> TYPE: DNA
<213> ORGANISM: Artificial Sequence
<220> FEATURE:
<223> OTHER INFORMATION: Oligonucleotide

<400> SEQUENCE: 31
agctgccacc                                                              10

<210> SEQ ID NO 32
<211> LENGTH: 10
<212> TYPE: DNA
<213> ORGANISM: Artificial Sequence
<220> FEATURE:
<223> OTHER INFORMATION: Oligonucleotide
```

```
<400> SEQUENCE: 32
agctgccact                                                          10

<210> SEQ ID NO 33
<211> LENGTH: 15
<212> TYPE: DNA
<213> ORGANISM: Artificial Sequence
<220> FEATURE:
<223> OTHER INFORMATION: Oligonucleotide

<400> SEQUENCE: 33
gcggaggccc caggt                                                    15

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide

<400> SEQUENCE: 34
accaagaggg aagaagcaca g                                             21

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide

<400> SEQUENCE: 35
ccaatgacgg acaggagaaa                                               20

<210> SEQ ID NO 36
<211> LENGTH: 11
<212> TYPE: DNA
<213> ORGANISM: Artificial Sequence
<220> FEATURE:
<223> OTHER INFORMATION: Oligonucleotide

<400> SEQUENCE: 36
gagctggtga g                                                        11

<210> SEQ ID NO 37
<211> LENGTH: 11
<212> TYPE: DNA
<213> ORGANISM: Artificial Sequence
<220> FEATURE:
<223> OTHER INFORMATION: Oligonucleotide

<400> SEQUENCE: 37
gagctggtga a                                                        11

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
ctgcactccg ttctgctcct                                               20

<210> SEQ ID NO 39
<211> LENGTH: 21
<212> TYPE: DNA
```

```
<213> ORGANISM: Artificial Sequence
<220> FEATURE:
<223> OTHER INFORMATION: Oligonucleotide

<400> SEQUENCE: 39 gatggggtc ctggtatgtc t                                            21

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide

<400> SEQUENCE: 40
ctggaggtca cggctcaag                                              19

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide

<400> SEQUENCE: 41
gtgtggcatg gaccttgtct g                                           21

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide

<400> SEQUENCE: 42
gcaatgcgcc gtatttgttt c                                           21

<210> SEQ ID NO 43
<211> LENGTH: 15
<212> TYPE: DNA
<213> ORGANISM: Artificial Sequence
<220> FEATURE:
<223> OTHER INFORMATION: Oligonucleotide

<400> SEQUENCE: 43
aaagcttatt acaga                                                  15

<210> SEQ ID NO 44
<211> LENGTH: 13
<212> TYPE: DNA
<213> ORGANISM: Artificial Sequence
<220> FEATURE:
<223> OTHER INFORMATION: Oligonucleotide

<400> SEQUENCE: 44
agcttattac agc                                                    13

<210> SEQ ID NO 45
<211> LENGTH: 23
<212> TYPE: DNA
<213> ORGANISM: Artificial Sequence
<220> FEATURE:
<223> OTHER INFORMATION: Oligonucleotide

<400> SEQUENCE: 45
ggatgagatg gcatatgtcc tgc                                         23
```

```
<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46
cctgtttcct gtcgctgctc                                              20

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide

<400> SEQUENCE: 47
ccaatacctg tccacgctga t                                            21

<210> SEQ ID NO 48
<211> LENGTH: 11
<212> TYPE: DNA
<213> ORGANISM: Artificial Sequence
<220> FEATURE:
<223> OTHER INFORMATION: Oligonucleotide

<400> SEQUENCE: 48
ggtgtcggaa c                                                       11

<210> SEQ ID NO 49
<211> LENGTH: 11
<212> TYPE: DNA
<213> ORGANISM: Artificial Sequence
<220> FEATURE:
<223> OTHER INFORMATION: Oligonucleotide

<400> SEQUENCE: 49
ggtgtcggaa a                                                       11

<210> SEQ ID NO 50
<211> LENGTH: 21
<212> TYPE: DNA
<213> ORGANISM: Artificial Sequence
<220> FEATURE:
<223> OTHER INFORMATION: Oligonucleotide

<400> SEQUENCE: 50
ctgataacgg cagcacagac c                                            21

<210> SEQ ID NO 51
<211> LENGTH: 17
<212> TYPE: DNA
<213> ORGANISM: Artificial Sequence
<220> FEATURE:
<223> OTHER INFORMATION: Oligonucleotide

<400> SEQUENCE: 51
gggctggtgg tggagag                                                 17

<210> SEQ ID NO 52
<211> LENGTH: 21
<212> TYPE: DNA
<213> ORGANISM: Artificial Sequence
<220> FEATURE:
<223> OTHER INFORMATION: Oligonucleotide
```

```
<400> SEQUENCE: 52
tctgacacag ccaaggagat g                                              21

<210> SEQ ID NO 53
<211> LENGTH: 9
<212> TYPE: DNA
<213> ORGANISM: Artificial Sequence
<220> FEATURE:
<223> OTHER INFORMATION: Oligonucleotide

<400> SEQUENCE: 53 ccaggagcg                                                             9

<210> SEQ ID NO 54
<211> LENGTH: 10
<212> TYPE: DNA
<213> ORGANISM: Artificial Sequence
<220> FEATURE:
<223> OTHER INFORMATION: Oligonucleotide

<400> SEQUENCE: 54
cccaggagcc                                                           10

<210> SEQ ID NO 55
<211> LENGTH: 19
<212> TYPE: DNA
<213> ORGANISM: Artificial Sequence
<220> FEATURE:
<223> OTHER INFORMATION: Oligonucleotide

<400> SEQUENCE: 55
tggacaggat gagcagcga                                                 19

<210> SEQ ID NO 56
<211> LENGTH: 17
<212> TYPE: DNA
<213> ORGANISM: Artificial Sequence
<220> FEATURE:
<223> OTHER INFORMATION: Oligonucleotide

<400> SEQUENCE: 56
gggctggtgg tggagag                                                   17

<210> SEQ ID NO 57
<211> LENGTH: 21
<212> TYPE: DNA
<213> ORGANISM: Artificial Sequence
<220> FEATURE:
<223> OTHER INFORMATION: Oligonucleotide

<400> SEQUENCE: 57
tctgacacag ccaaggagat g                                              21

<210> SEQ ID NO 58
<211> LENGTH: 10
<212> TYPE: DNA
<213> ORGANISM: Artificial Sequence
<220> FEATURE:
<223> OTHER INFORMATION: Oligonucleotide

<400> SEQUENCE: 58
ccaggagcgt                                                           10

<210> SEQ ID NO 59
<211> LENGTH: 10
<212> TYPE: DNA
```

```
<213> ORGANISM: Artificial Sequence
<220> FEATURE:
<223> OTHER INFORMATION: Oligonucleotide

<400> SEQUENCE: 59
ccaggagcgg                                                           10

<210> SEQ ID NO 60
<211> LENGTH: 20
<212> TYPE: DNA
<213> ORGANISM: Artficial Sequence

<400> SEQUENCE: 60
ggacaggatg agcagcgaca                                                20

<210> SEQ ID NO 61
<211> LENGTH: 21
<212> TYPE: DNA
<213> ORGANISM: Artificial Sequence
<220> FEATURE:
<223> OTHER INFORMATION: Oligonucleotide

<400> SEQUENCE: 61
tctccacagc actcccgaca g                                              21

<210> SEQ ID NO 62
<211> LENGTH: 21
<212> TYPE: DNA
<213> ORGANISM: Artificial Sequence
<220> FEATURE:
<223> OTHER INFORMATION: Oligonucleotide

<400> SEQUENCE: 62
ccgagaacaa tggcgagcat c                                              21

<210> SEQ ID NO 63
<211> LENGTH: 9
<212> TYPE: DNA
<213> ORGANISM: Artificial Sequence
<220> FEATURE:
<223> OTHER INFORMATION: Oligonucleotide

<400> SEQUENCE: 63 ggtccgggt                                                             9

<210> SEQ ID NO 64
<211> LENGTH: 9
<212> TYPE: DNA
<213> ORGANISM: Artificial Sequence
<220> FEATURE:
<223> OTHER INFORMATION: Oligonucleotide

<400> SEQUENCE: 64 ggtccgggc                                                             9

<210> SEQ ID NO 65
<211> LENGTH: 21
<212> TYPE: DNA
<213> ORGANISM: Artificial Sequence
<220> FEATURE:
<223> OTHER INFORMATION: Oligonucleotide

<400> SEQUENCE: 65
tttgccattg ggcatggtct g                                              21

<210> SEQ ID NO 66
```

```
<211> LENGTH: 18
<212> TYPE: DNA
<213> ORGANISM: Artificial Sequence
<220> FEATURE:
<223> OTHER INFORMATION: Oligonucleotide

<400> SEQUENCE: 66
caccagccca cccgagag                                              18

<210> SEQ ID NO 67
<211> LENGTH: 21
<212> TYPE: DNA
<213> ORGANISM: Artificial Sequence
<220> FEATURE:
<223> OTHER INFORMATION: Oligonucleotide

<400> SEQUENCE: 67
accgagaaca atggcgagca t                                          21

<210> SEQ ID NO 68
<211> LENGTH: 10
<212> TYPE: DNA
<213> ORGANISM: Artificial Sequence
<220> FEATURE:
<223> OTHER INFORMATION: Oligonucleotide

<400> SEQUENCE: 68
ccatggtggg                                                       10

<210> SEQ ID NO 69
<211> LENGTH: 10
<212> TYPE: DNA
<213> ORGANISM: Artificial Sequence
<220> FEATURE:
<223> OTHER INFORMATION: Oligonucleotide

<400> SEQUENCE: 69
ccatggtggc                                                       10

<210> SEQ ID NO 70
<211> LENGTH: 17
<212> TYPE: DNA
<213> ORGANISM: Artificial Sequence
<220> FEATURE:
<223> OTHER INFORMATION: Oligonucleotide

<400> SEQUENCE: 70
acgggtcggg gagagtc                                               17

<210> SEQ ID NO 71
<211> LENGTH: 18
<212> TYPE: DNA
<213> ORGANISM: Artificial Sequence
<220> FEATURE:
<223> OTHER INFORMATION: Oligonucleotide

<400> SEQUENCE: 71
ccggtacagc cccatccc                                              18

<210> SEQ ID NO 72
<211> LENGTH: 21
<212> TYPE: DNA
<213> ORGANISM: Artificial Sequence
<220> FEATURE:
<223> OTHER INFORMATION: Oligonucleotide

<400> SEQUENCE: 72
```

```
gccgactcac cgagaacaat g                                              21

<210> SEQ ID NO 73
<211> LENGTH: 9
<212> TYPE: DNA
<213> ORGANISM: Artificial Sequence
<220> FEATURE:
<223> OTHER INFORMATION: Oligonucleotide

<400> SEQUENCE: 73 gtgggacgg                                                             9

<210> SEQ ID NO 74
<211> LENGTH: 10
<212> TYPE: DNA
<213> ORGANISM: Artificial Sequence
<220> FEATURE:
<223> OTHER INFORMATION: Oligonucleotide

<400> SEQUENCE: 74
ggtgggacga                                                           10

<210> SEQ ID NO 75
<211> LENGTH: 19
<212> TYPE: DNA
<213> ORGANISM: Artificial Sequence
<220> FEATURE:
<223> OTHER INFORMATION: Oligonucleotide

<400> SEQUENCE: 75
gtcggggaga gtcagctgg                                                 19

<210> SEQ ID NO 76
<211> LENGTH: 22
<212> TYPE: DNA
<213> ORGANISM: Artificial Sequence
<220> FEATURE:
<223> OTHER INFORMATION: Oligonucleotide

<400> SEQUENCE: 76
ggggacagga gggagggttg ag                                             22

<210> SEQ ID NO 77
<211> LENGTH: 25
<212> TYPE: DNA
<213> ORGANISM: Artificial Sequence
<220> FEATURE:
<223> OTHER INFORMATION: Oligonucleotide

<400> SEQUENCE: 77
gaagaggagt gggcaggaga tggtg                                          25

<210> SEQ ID NO 78
<211> LENGTH: 12
<212> TYPE: DNA
<213> ORGANISM: Artificial Sequence
<220> FEATURE:
<223> OTHER INFORMATION: Oligonucleotide

<400> SEQUENCE: 78
ggagatcatg ac                                                        12

<210> SEQ ID NO 79
<211> LENGTH: 13
<212> TYPE: DNA
<213> ORGANISM: Artificial Sequence
<220> FEATURE:
```

```
<223> OTHER INFORMATION: Oligonucleotide

<400> SEQUENCE: 79
tggagatcat gat                                                        13

<210> SEQ ID NO 80
<211> LENGTH: 16
<212> TYPE: DNA
<213> ORGANISM: Artificial Sequence
<220> FEATURE:
<223> OTHER INFORMATION: Oligonucleotide

<400> SEQUENCE: 80
ggtgacccgg cgcttg                                                     16

<210> SEQ ID NO 81
<211> LENGTH: 20
<212> TYPE: DNA
<213> ORGANISM: Artificial Sequence
<220> FEATURE:
<223> OTHER INFORMATION: Oligonucleotide

<400> SEQUENCE: 81
agcaaccaag ccccaaagag                                                 20

<210> SEQ ID NO 82
<211> LENGTH: 19
<212> TYPE: DNA
<213> ORGANISM: Artificial Sequence
<220> FEATURE:
<223> OTHER INFORMATION: Oligonucleotide

<400> SEQUENCE: 82
gagcgcgcag taggagagg                                                  19

<210> SEQ ID NO 83
<211> LENGTH: 11
<212> TYPE: DNA
<213> ORGANISM: Artificial Sequence
<220> FEATURE:
<223> OTHER INFORMATION: Oligonucleotide

<400> SEQUENCE: 83
ttcaggtggc t                                                          11

<210> SEQ ID NO 84
<211> LENGTH: 10
<212> TYPE: DNA
<213> ORGANISM: Artificial Sequence
<220> FEATURE:
<223> OTHER INFORMATION: Oligonucleotide

<400> SEQUENCE: 84
tcaggtggcc                                                            10

<210> SEQ ID NO 85
<211> LENGTH: 21
<212> TYPE: DNA
<213> ORGANISM: Artificial Sequence
<220> FEATURE:
<223> OTHER INFORMATION: Oligonucleotide

<400> SEQUENCE: 85
actcagctgg ctcagagatg c                                               21

<210> SEQ ID NO 86
```

```
<211> LENGTH: 21
<212> TYPE: DNA
<213> ORGANISM: Artificial Sequence
<220> FEATURE:
<223> OTHER INFORMATION: Oligonucleotide

<400> SEQUENCE: 86
cgctacaacc ggcagggtgg g                                              21

<210> SEQ ID NO 87
<211> LENGTH: 21
<212> TYPE: DNA
<213> ORGANISM: Artificial Sequence
<220> FEATURE:
<223> OTHER INFORMATION: Oligonucleotide

<400> SEQUENCE: 87
gcagcatgag cgggcagggt a                                              21

<210> SEQ ID NO 88
<211> LENGTH: 11
<212> TYPE: DNA
<213> ORGANISM: Artificial Sequence
<220> FEATURE:
<223> OTHER INFORMATION: Oligonucleotide

<400> SEQUENCE: 88
ggacgagtag a                                                         11

<210> SEQ ID NO 89
<211> LENGTH: 11
<212> TYPE: DNA
<213> ORGANISM: Artificial Sequence
<220> FEATURE:
<223> OTHER INFORMATION: Oligonucleotide

<400> SEQUENCE: 89
ggacgagtag c                                                         11

<210> SEQ ID NO 90
<211> LENGTH: 19
<212> TYPE: DNA
<213> ORGANISM: Artificial Sequence
<220> FEATURE:
<223> OTHER INFORMATION: Oligonucleotide

<400> SEQUENCE: 90
ccacgtagtc gcggtcctc                                                 19

<210> SEQ ID NO 91
<211> LENGTH: 19
<212> TYPE: DNA
<213> ORGANISM: Artificial Sequence
<220> FEATURE:
<223> OTHER INFORMATION: Oligonucleotide

<400> SEQUENCE: 91
cgccttcccc cacgccacc                                                 19

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide

<400> SEQUENCE: 92
```
gttggagccg caggggtccg                                              20

<210> SEQ ID NO 93
<211> LENGTH: 8
<212> TYPE: DNA
<213> ORGANISM: Artificial Sequence
<220> FEATURE:
<223> OTHER INFORMATION: Oligonucleotide

<400> SEQUENCE: 93 ggcgcggg                                                            8

<210> SEQ ID NO 94
<211> LENGTH: 8
<212> TYPE: DNA
<213> ORGANISM: Artificial Sequence
<220> FEATURE:
<223> OTHER INFORMATION: Oligonucleotide

<400> SEQUENCE: 94 ggcgcggc                                                            8

<210> SEQ ID NO 95
<211> LENGTH: 15
<212> TYPE: DNA
<213> ORGANISM: Artificial Sequence
<220> FEATURE:
<223> OTHER INFORMATION: Oligonucleotide

<400> SEQUENCE: 95
gggcgcacag tcggg                                                   15

<210> SEQ ID NO 96
<211> LENGTH: 20
<212> TYPE: DNA
<213> ORGANISM: Artificial Sequence
<220> FEATURE:
<223> OTHER INFORMATION: Oligonucleotide

<400> SEQUENCE: 96
tgcggttttc catcaagaag                                              20

<210> SEQ ID NO 97
<211> LENGTH: 18
<212> TYPE: DNA
<213> ORGANISM: Artificial Sequence
<220> FEATURE:
<223> OTHER INFORMATION: Oligonucleotide

<400> SEQUENCE: 97
ggagttggcc cagcagaa                                                18

<210> SEQ ID NO 98
<211> LENGTH: 10
<212> TYPE: DNA
<213> ORGANISM: Artificial Sequence
<220> FEATURE:
<223> OTHER INFORMATION: Oligonucleotide

<400> SEQUENCE: 98
ccgacagggt                                                         10

<210> SEQ ID NO 99
<211> LENGTH: 9
<212> TYPE: DNA
<213> ORGANISM: Artificial Sequence
<220> FEATURE:

<223> OTHER INFORMATION: Oligonucleotide

<400> SEQUENCE: 99 cgacagggg                                                              9

<210> SEQ ID NO 100
<211> LENGTH: 27
<212> TYPE: DNA
<213> ORGANISM: Artificial Sequence
<220> FEATURE:
<223> OTHER INFORMATION: Oligonucleotide

<400> SEQUENCE: 100
cttgagaacc ttggtctcct tcttgat                                         27

<210> SEQ ID NO 101
<211> LENGTH: 18
<212> TYPE: DNA
<213> ORGANISM: Artificial Sequence
<220> FEATURE:
<223> OTHER INFORMATION: Oligonucleotide

<400> SEQUENCE: 101
caacgccgac ttctggaa                                                  18

<210> SEQ ID NO 102
<211> LENGTH: 21
<212> TYPE: DNA
<213> ORGANISM: Artificial Sequence
<220> FEATURE:
<223> OTHER INFORMATION: Oligonucleotide

<400> SEQUENCE: 102
acatgcgatc gaaaggactc t                                              21

<210> SEQ ID NO 103
<211> LENGTH: 10
<212> TYPE: DNA
<213> ORGANISM: Artificial Sequence
<220> FEATURE:
<223> OTHER INFORMATION: Oligonucleotide

<400> SEQUENCE: 103
cgggggaac                                                            10

<210> SEQ ID NO 104
<211> LENGTH: 10
<212> TYPE: DNA
<213> ORGANISM: Artificial Sequence
<220> FEATURE:
<223> OTHER INFORMATION: Oligonucleotide

<400> SEQUENCE: 104
cgggggaat                                                            10

<210> SEQ ID NO 105
<211> LENGTH: 19
<212> TYPE: DNA
<213> ORGANISM: Artificial Sequence
<220> FEATURE:
<223> OTHER INFORMATION: Oligonucleotide

<400> SEQUENCE: 105
ggcgttgggc atcatgtgg                                                 19

<210> SEQ ID NO 106

```
<211> LENGTH: 18
<212> TYPE: DNA
<213> ORGANISM: Artificial Sequence
<220> FEATURE:
<223> OTHER INFORMATION: Oligonucleotide

<400> SEQUENCE: 106
gcagtccagc ccgaaatg                                                 18

<210> SEQ ID NO 107
<211> LENGTH: 16
<212> TYPE: DNA
<213> ORGANISM: Artificial Sequence
<220> FEATURE:
<223> OTHER INFORMATION: Oligonucleotide

<400> SEQUENCE: 107
gcacgatggc tgcgga                                                   16

<210> SEQ ID NO 108
<211> LENGTH: 10
<212> TYPE: DNA
<213> ORGANISM: Artificial Sequence
<220> FEATURE:
<223> OTHER INFORMATION: Oligonucleotide

<400> SEQUENCE: 108
ctgcggacac                                                          10

<210> SEQ ID NO 109
<211> LENGTH: 10
<212> TYPE: DNA
<213> ORGANISM: Artificial Sequence
<220> FEATURE:
<223> OTHER INFORMATION: Oligonucleotide

<400> SEQUENCE: 109
ctgcggacat                                                          10

<210> SEQ ID NO 110
<211> LENGTH: 15
<212> TYPE: DNA
<213> ORGANISM: Artificial Sequence
<220> FEATURE:
<223> OTHER INFORMATION: Oligonucleotide

<400> SEQUENCE: 110
cagcacgttg cccag                                                    15

<210> SEQ ID NO 111
<211> LENGTH: 13
<212> TYPE: DNA
<213> ORGANISM: Artificial Sequence
<220> FEATURE:
<223> OTHER INFORMATION: Oligonucleotide

<400> SEQUENCE: 111
caacgtgctg gtg                                                      13

<210> SEQ ID NO 112
<211> LENGTH: 15
<212> TYPE: DNA
<213> ORGANISM: Artificial Sequence
<220> FEATURE:
<223> OTHER INFORMATION: Oligonucleotide

<400> SEQUENCE: 112
```

-continued catcttgcgc ttgta                                                    15

<210> SEQ ID NO 113
<211> LENGTH: 8
<212> TYPE: DNA
<213> ORGANISM: Artificial Sequence
<220> FEATURE:
<223> OTHER INFORMATION: Oligonucleotide

<400> SEQUENCE: 113 ggctgcgc                                                             8

<210> SEQ ID NO 114
<211> LENGTH: 9
<212> TYPE: DNA
<213> ORGANISM: Artificial Sequence
<220> FEATURE:
<223> OTHER INFORMATION: Oligonucleotide

<400> SEQUENCE: 114 tggctgcgg                                                            9

<210> SEQ ID NO 115
<211> LENGTH: 17
<212> TYPE: DNA
<213> ORGANISM: Artificial Sequence
<220> FEATURE:
<223> OTHER INFORMATION: Oligonucleotide

<400> SEQUENCE: 115
acaccagcac gttgccc                                                  17

<210> SEQ ID NO 116
<211> LENGTH: 16
<212> TYPE: DNA
<213> ORGANISM: Artificial Sequence
<220> FEATURE:
<223> OTHER INFORMATION: Oligonucleotide

<400> SEQUENCE: 116
cgccaagatg accaac                                                   16

<210> SEQ ID NO 117
<211> LENGTH: 17
<212> TYPE: DNA
<213> ORGANISM: Artificial Sequence
<220> FEATURE:
<223> OTHER INFORMATION: Oligonucleotide

<400> SEQUENCE: 117
cggaatgaag gagatga                                                  17

<210> SEQ ID NO 118
<211> LENGTH: 10
<212> TYPE: DNA
<213> ORGANISM: Artificial Sequence
<220> FEATURE:
<223> OTHER INFORMATION: Oligonucleotide

<400> SEQUENCE: 118
gccacgaaga                                                          10

<210> SEQ ID NO 119
<211> LENGTH: 10
<212> TYPE: DNA
<213> ORGANISM: Artificial Sequence
<220> FEATURE:

<223> OTHER INFORMATION: Oligonucleotide

<400> SEQUENCE: 119
gccacgaagc 10

<210> SEQ ID NO 120
<211> LENGTH: 21
<212> TYPE: DNA
<213> ORGANISM: Artificial Sequence
<220> FEATURE:
<223> OTHER INFORMATION: Oligonucleotide

<400> SEQUENCE: 120
ggtctgacac agccagagac a 21

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide

<400> SEQUENCE: 121
gcagctgcct acatccacat 20

<210> SEQ ID NO 122
<211> LENGTH: 21
<212> TYPE: DNA
<213> ORGANISM: Artificial Sequence
<220> FEATURE:
<223> OTHER INFORMATION: Oligonucleotide

<400> SEQUENCE: 122
cattcggggt gaaaggtgtt a 21

<210> SEQ ID NO 123
<211> LENGTH: 10
<212> TYPE: DNA
<213> ORGANISM: Artificial Sequence
<220> FEATURE:
<223> OTHER INFORMATION: Oligonucleotide

<400> SEQUENCE: 123
gtccagctcc 10

<210> SEQ ID NO 124
<211> LENGTH: 10
<212> TYPE: DNA
<213> ORGANISM: Artificial Sequence
<220> FEATURE:
<223> OTHER INFORMATION: Oligonucleotide

<400> SEQUENCE: 124
gtccagctct 10

<210> SEQ ID NO 125
<211> LENGTH: 23
<212> TYPE: DNA
<213> ORGANISM: Artificial Sequence
<220> FEATURE:
<223> OTHER INFORMATION: Oligonucleotide

<400> SEQUENCE: 125
cagacagact ctgcaacagg gtc 23

<210> SEQ ID NO 126

```
<211> LENGTH: 21
<212> TYPE: DNA
<213> ORGANISM: Artificial Sequence
<220> FEATURE:
<223> OTHER INFORMATION: Oligonucleotide

<400> SEQUENCE: 126
ggagagtcgg ggagcaggaa c                                               21

<210> SEQ ID NO 127
<211> LENGTH: 17
<212> TYPE: DNA
<213> ORGANISM: Artificial Sequence
<220> FEATURE:
<223> OTHER INFORMATION: Oligonucleotide

<400> SEQUENCE: 127
gaggcggggg cacaagg                                                    17

<210> SEQ ID NO 128
<211> LENGTH: 11
<212> TYPE: DNA
<213> ORGANISM: Artificial Sequence
<220> FEATURE:
<223> OTHER INFORMATION: Oligonucleotide

<400> SEQUENCE: 128
gcacagagca c                                                          11

<210> SEQ ID NO 129
<211> LENGTH: 11
<212> TYPE: DNA
<213> ORGANISM: Artificial Sequence
<220> FEATURE:
<223> OTHER INFORMATION: Oligonucleotide

<400> SEQUENCE: 129
gcacagagca t                                                          11

<210> SEQ ID NO 130
<211> LENGTH: 18
<212> TYPE: DNA
<213> ORGANISM: Artificial Sequence
<220> FEATURE:
<223> OTHER INFORMATION: Oligonucleotide

<400> SEQUENCE: 130
ccccagcctt gctctcca                                                   18

<210> SEQ ID NO 131
<211> LENGTH: 21
<212> TYPE: DNA
<213> ORGANISM: Artificial Sequence
<220> FEATURE:
<223> OTHER INFORMATION: Oligonucleotide

<400> SEQUENCE: 131
ctacatcccg ctgctgctca t                                               21

<210> SEQ ID NO 132
<211> LENGTH: 19
<212> TYPE: DNA
<213> ORGANISM: Artificial Sequence
<220> FEATURE:
<223> OTHER INFORMATION: Oligonucleotide

<400> SEQUENCE: 132
```

-continued

```
cctgctcccc gactctcca                                                19

<210> SEQ ID NO 133
<211> LENGTH: 9
<212> TYPE: DNA
<213> ORGANISM: Artificial Sequence
<220> FEATURE:
<223> OTHER INFORMATION: Oligonucleotide

<400> SEQUENCE: 133 gcgcagctc                                                            9

<210> SEQ ID NO 134
<211> LENGTH: 9
<212> TYPE: DNA
<213> ORGANISM: Artificial Sequence
<220> FEATURE:
<223> OTHER INFORMATION: Oligonucleotide

<400> SEQUENCE: 134 gcgcagcta                                                            9

<210> SEQ ID NO 135
<211> LENGTH: 24
<212> TYPE: DNA
<213> ORGANISM: Artificial Sequence
<220> FEATURE:
<223> OTHER INFORMATION: Oligonucleotide

<400> SEQUENCE: 135
ggaatatgcg cccatagaga acca                                          24

<210> SEQ ID NO 136
<211> LENGTH: 25
<212> TYPE: DNA
<213> ORGANISM: Artificial Sequence
<220> FEATURE:
<223> OTHER INFORMATION: Oligonucleotide

<400> SEQUENCE: 136
gctcacttgg cttattggct tcctc                                         25

<210> SEQ ID NO 137
<211> LENGTH: 20
<212> TYPE: DNA
<213> ORGANISM: Artificial Sequence
<220> FEATURE:
<223> OTHER INFORMATION: Oligonucleotide

<400> SEQUENCE: 137
catgagcagc agcgggatgt                                               20

<210> SEQ ID NO 138
<211> LENGTH: 10
<212> TYPE: DNA
<213> ORGANISM: Artificial Sequence
<220> FEATURE:
<223> OTHER INFORMATION: Oligonucleotide

<400> SEQUENCE: 138
catgcgtcgg                                                          10

<210> SEQ ID NO 139
<211> LENGTH: 10
<212> TYPE: DNA
<213> ORGANISM: Artificial Sequence
<220> FEATURE:
```

<223> OTHER INFORMATION: Oligonucleotide

<400> SEQUENCE: 139
catgcgtcga          10

<210> SEQ ID NO 140
<211> LENGTH: 18
<212> TYPE: DNA
<213> ORGANISM: Artificial Sequence
<220> FEATURE:
<223> OTHER INFORMATION: Oligonucleotide

<400> SEQUENCE: 140
ggtccgagcg gtcttccg          18

<210> SEQ ID NO 141
<211> LENGTH: 24
<212> TYPE: DNA
<213> ORGANISM: Artificial Sequence
<220> FEATURE:
<223> OTHER INFORMATION: Oligonucleotide

<400> SEQUENCE: 141
agggcaacaa caccacatca ccac          24

<210> SEQ ID NO 142
<211> LENGTH: 22
<212> TYPE: DNA
<213> ORGANISM: Artificial Sequence
<220> FEATURE:
<223> OTHER INFORMATION: Oligonucleotide

<400> SEQUENCE: 142
gcagcaccaa caccgacacc at          22

<210> SEQ ID NO 143
<211> LENGTH: 11
<212> TYPE: DNA
<213> ORGANISM: Artificial Sequence
<220> FEATURE:
<223> OTHER INFORMATION: Oligonucleotide

<400> SEQUENCE: 143
acgtcggaga t          11

<210> SEQ ID NO 144
<211> LENGTH: 10
<212> TYPE: DNA
<213> ORGANISM: Artificial Sequence
<220> FEATURE:
<223> OTHER INFORMATION: Oligonucleotide

<400> SEQUENCE: 144
cgtcggagac          10

<210> SEQ ID NO 145
<211> LENGTH: 19
<212> TYPE: DNA
<213> ORGANISM: Artificial Sequence
<220> FEATURE:
<223> OTHER INFORMATION: Oligonucleotide

<400> SEQUENCE: 145
accagtagtg ttgccgccg          19

<210> SEQ ID NO 146

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 146
tcagggcaac aacaccacat                                              20

<210> SEQ ID NO 147
<211> LENGTH: 18
<212> TYPE: DNA
<213> ORGANISM: Artificial Sequence
<220> FEATURE:
<223> OTHER INFORMATION: Oligonucleotide

<400> SEQUENCE: 147
gcaccaacac cgacacca                                                18

<210> SEQ ID NO 148
<211> LENGTH: 9
<212> TYPE: DNA
<213> ORGANISM: Artificial Sequence
<220> FEATURE:
<223> OTHER INFORMATION: Oligonucleotide

<400> SEQUENCE: 148 gttgccgcc                                                           9

<210> SEQ ID NO 149
<211> LENGTH: 9
<212> TYPE: DNA
<213> ORGANISM: Artificial Sequence
<220> FEATURE:
<223> OTHER INFORMATION: Oligonucleotide

<400> SEQUENCE: 149 gttgccgct                                                           9

<210> SEQ ID NO 150
<211> LENGTH: 19
<212> TYPE: DNA
<213> ORGANISM: Artificial Sequence
<220> FEATURE:
<223> OTHER INFORMATION: Oligonucleotide

<400> SEQUENCE: 150
ggtctcaaag ggagccggt                                               19

<210> SEQ ID NO 151
<211> LENGTH: 20
<212> TYPE: DNA
<213> ORGANISM: Artificial Sequence
<220> FEATURE:
<223> OTHER INFORMATION: Oligonucleotide

<400> SEQUENCE: 151
ttttcttccc tccccttcc                                               20

<210> SEQ ID NO 152
<211> LENGTH: 17
<212> TYPE: DNA
<213> ORGANISM: Artificial Sequence
<220> FEATURE:
<223> OTHER INFORMATION: Oligonucleotide

<400> SEQUENCE: 152
```

```
ccaccacgca cgcattg                                                    17

<210> SEQ ID NO 153
<211> LENGTH: 10
<212> TYPE: DNA
<213> ORGANISM: Artificial Sequence
<220> FEATURE:
<223> OTHER INFORMATION: Oligonucleotide

<400> SEQUENCE: 153
aagggagccg                                                            10

<210> SEQ ID NO 154
<211> LENGTH: 11
<212> TYPE: DNA
<213> ORGANISM: Artificial Sequence
<220> FEATURE:
<223> OTHER INFORMATION: Oligonucleotide

<400> SEQUENCE: 154
aaagggagcc a                                                          11

<210> SEQ ID NO 155
<211> LENGTH: 22
<212> TYPE: DNA
<213> ORGANISM: Artificial Sequence
<220> FEATURE:
<223> OTHER INFORMATION: Oligonucleotide

<400> SEQUENCE: 155
gtggtgatgt ggtgttgttg cc                                              22

<210> SEQ ID NO 156
<211> LENGTH: 21
<212> TYPE: DNA
<213> ORGANISM: Artificial Sequence
<220> FEATURE:
<223> OTHER INFORMATION: Oligonucleotide

<400> SEQUENCE: 156
gctcaactac gaactcccta a                                               21

<210> SEQ ID NO 157
<211> LENGTH: 21
<212> TYPE: DNA
<213> ORGANISM: Artificial Sequence
<220> FEATURE:
<223> OTHER INFORMATION: Oligonucleotide

<400> SEQUENCE: 157
tcactacggc tgtcagtaaa g                                               21

<210> SEQ ID NO 158
<211> LENGTH: 12
<212> TYPE: DNA
<213> ORGANISM: Artificial Sequence
<220> FEATURE:
<223> OTHER INFORMATION: Oligonucleotide

<400> SEQUENCE: 158
ttagcttctc ca                                                         12

<210> SEQ ID NO 159
<211> LENGTH: 12
<212> TYPE: DNA
<213> ORGANISM: Artificial Sequence
<220> FEATURE:
```

<223> OTHER INFORMATION: Oligonucleotide

<400> SEQUENCE: 159
ttagcttctc cg                                                           12

<210> SEQ ID NO 160
<211> LENGTH: 29
<212> TYPE: DNA
<213> ORGANISM: Artificial Sequence
<220> FEATURE:
<223> OTHER INFORMATION: Oligonucleotide

<400> SEQUENCE: 160
gagttaaagt cattactgta gagcctggt                                         29

<210> SEQ ID NO 161
<211> LENGTH: 16
<212> TYPE: DNA
<213> ORGANISM: Artificial Sequence
<220> FEATURE:
<223> OTHER INFORMATION: Oligonucleotide

<400> SEQUENCE: 161
gctctgctcg ctcaac                                                       16

<210> SEQ ID NO 162
<211> LENGTH: 21
<212> TYPE: DNA
<213> ORGANISM: Artificial Sequence
<220> FEATURE:
<223> OTHER INFORMATION: Oligonucleotide

<400> SEQUENCE: 162
gattttagtg gctttccttt c                                                 21

<210> SEQ ID NO 163
<211> LENGTH: 9
<212> TYPE: DNA
<213> ORGANISM: Artificial Sequence
<220> FEATURE:
<223> OTHER INFORMATION: Oligonucleotide

<400> SEQUENCE: 163 ccgagtgcg                                                                9

<210> SEQ ID NO 164
<211> LENGTH: 10
<212> TYPE: DNA
<213> ORGANISM: Artificial Sequence
<220> FEATURE:
<223> OTHER INFORMATION: Oligonucleotide

<400> SEQUENCE: 164
gccgagtgca                                                              10

<210> SEQ ID NO 165
<211> LENGTH: 18
<212> TYPE: DNA
<213> ORGANISM: Artificial Sequence
<220> FEATURE:
<223> OTHER INFORMATION: Oligonucleotide

<400> SEQUENCE: 165
agtgcccctc atggaggc                                                     18

<210> SEQ ID NO 166

```
<211> LENGTH: 25
<212> TYPE: DNA
<213> ORGANISM: Artificial Sequence
<220> FEATURE:
<223> OTHER INFORMATION: Oligonucleotide

<400> SEQUENCE: 166 ctcaattta aactttggtt gctta                                           25

<210> SEQ ID NO 167
<211> LENGTH: 23
<212> TYPE: DNA
<213> ORGANISM: Artificial Sequence
<220> FEATURE:
<223> OTHER INFORMATION: Oligonucleotide

<400> SEQUENCE: 167
ttttgaatag gaaacaccca taa                                            23

<210> SEQ ID NO 168
<211> LENGTH: 11
<212> TYPE: DNA
<213> ORGANISM: Artificial Sequence
<220> FEATURE:
<223> OTHER INFORMATION: Oligonucleotide

<400> SEQUENCE: 168
gcattcctca g                                                         11

<210> SEQ ID NO 169
<211> LENGTH: 11
<212> TYPE: DNA
<213> ORGANISM: Artificial Sequence
<220> FEATURE:
<223> OTHER INFORMATION: Oligonucleotide

<400> SEQUENCE: 169
gcattcctca c                                                         11

<210> SEQ ID NO 170
<211> LENGTH: 28
<212> TYPE: DNA
<213> ORGANISM: Artificial Sequence
<220> FEATURE:
<223> OTHER INFORMATION: Oligonucleotide

<400> SEQUENCE: 170
gttcaccatg attgcttcag tcttaagc                                       28

<210> SEQ ID NO 171
<211> LENGTH: 30
<212> TYPE: DNA
<213> ORGANISM: Artificial Sequence
<220> FEATURE:
<223> OTHER INFORMATION: Oligonucleotide

<400> SEQUENCE: 171
atgatgacaa tgatgctgat gatgataatg                                     30

<210> SEQ ID NO 172
<211> LENGTH: 25
<212> TYPE: DNA
<213> ORGANISM: Artificial Sequence
<220> FEATURE:
<223> OTHER INFORMATION: Oligonucleotide

<400> SEQUENCE: 172
```
tccaccatcg gaggtattga aaatg                                          25

<210> SEQ ID NO 173
<211> LENGTH: 15
<212> TYPE: DNA
<213> ORGANISM: Artificial Sequence
<220> FEATURE:
<223> OTHER INFORMATION: Oligonucleotide

<400> SEQUENCE: 173
tcacagaaat atcac                                                     15

<210> SEQ ID NO 174
<211> LENGTH: 14
<212> TYPE: DNA
<213> ORGANISM: Artificial Sequence
<220> FEATURE:
<223> OTHER INFORMATION: Oligonucleotide

<400> SEQUENCE: 174
cacagaaata tcag                                                      14

<210> SEQ ID NO 175
<211> LENGTH: 26
<212> TYPE: DNA
<213> ORGANISM: Artificial Sequence
<220> FEATURE:
<223> OTHER INFORMATION: Oligonucleotide

<400> SEQUENCE: 175
attgccaaac caataggcca attagg                                         26

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
ggcttcagtt tcccgatctg                                                20

<210> SEQ ID NO 177
<211> LENGTH: 20
<212> TYPE: DNA
<213> ORGANISM: Artificial Sequence
<220> FEATURE:
<223> OTHER INFORMATION: Oligonucleotide

<400> SEQUENCE: 177
taggcaaggg caggcactac                                                20

<210> SEQ ID NO 178
<211> LENGTH: 10
<212> TYPE: DNA
<213> ORGANISM: Artificial Sequence
<220> FEATURE:
<223> OTHER INFORMATION: Oligonucleotide

<400> SEQUENCE: 178
aaggagctgg                                                           10

<210> SEQ ID NO 179
<211> LENGTH: 11
<212> TYPE: DNA
<213> ORGANISM: Artificial Sequence
<220> FEATURE:

```
<223> OTHER INFORMATION: Oligonucleotide

<400> SEQUENCE: 179
gaaggagctg a                                                          11

<210> SEQ ID NO 180
<211> LENGTH: 16
<212> TYPE: DNA
<213> ORGANISM: Artificial Sequence
<220> FEATURE:
<223> OTHER INFORMATION: Oligonucleotide

<400> SEQUENCE: 180
gtacatgggg gccccc                                                     16
```

METHODS FOR SELECTING MEDICATIONS

CROSS-REFERENCE TO RELATED APPLICATIONS

This application is a National Stage application under 35 U.S.C. §371 and claims benefit under 35 U.S.C. §119(a) of International Application No. PCT/US2004/005113 having an International Filing Date of Feb. 20, 2004, which claims the benefit of U.S. Provisional Application Ser. No. 60/448, 547, filed Feb. 20, 2003.

TECHNICAL FIELD

This invention relates to methods for selecting a medication (e.g., psychotropic medication) for a patient, and more particularly to selecting a patient's medication based on the genotype of genes encoding drug-metabolizing enzymes and genes encoding products involved in, for example, neurotransmission.

SUMMARY

The invention is based on the identification of a set of genes with polymorphisms that are associated with psychiatric diagnosis and pharmacological response to a medication. As a result, methods of the invention allow the genotype of a patient to be determined and, based on the genotype, a suitable medication to be selected for the patient. Methods of the invention allow the output of multiple genotypic assessments to be integrated, providing important and improved clinical information on which to select and dose medications. Thus, the methods of the invention provide a rational method for the identification of a medication that will result in an optimal response in the patient.

In one aspect, the invention features a method for selecting a psychotropic medication (e.g., an antidepressant, an antipsychotic agent, an antianxiety-sedative agent, or a mood-stabilizing agent) for a patient. The method includes providing the patient's genotype for a panel of genes, wherein the panel includes at least three cytochrome P450 genes and a serotonin transporter gene and selecting the psychotropic medication based on the genotype. The at least three cytochrome P450 genes can encode CYP2D6, 1A2, and 2C19 and providing the patient's genotype can include determining if the patient has the CYP1A2*1A or 1A2*3 allele, the CYP2C19*1A, 2C19*1B, or 2C19*2A allele, and the CYP2D6*1A, 2D6*2, 2D6*2N, 2D6*3, 2D6*4, 2D6*5, 2D6*6, 2D6*7, 2D6*8, 2D6*10, 2D6*12, or 2D6*17 allele.

The panel can include 4 cytochrome P450 genes (e.g., genes encoding CYP2D6, 2C19, 3A4, and 1A2). Providing the patient's genotype can include determining if said patient contains the CYP2D6*2, 2D6*3, 2D6*4, 2D6*10, or 2D6*17 allele, the CYP2C19*2A, 2C19*2B, 2C19*3, 2C19*4, 2C19*5A, 2C19*5B, 2C19*6, 2C19*7, or 2C19*8 allele, the CYP3A4*1B, 3A4*2, 3A4*5, 3A4*6, 3A4*12, 3A4*13, 3A4*15A, 3A4*17, 3A4*18A allele, and the CYP1A2*1F allele.

The panel can include at least 5 cytochrome P450 genes (e.g., CYP1A1, 1A2, 2D6, 2C19, and 3A4). Providing the patient's genotype can include determining if the patient has the CYP1A1*1A, 1A1*2, 1A1*3, or 1A1*4 allele, the CYP1A2*1A or 1A2*3 allele, the CYP2C19*1A, 2C19*1B, or 2C19*2A allele, the CYP2D6*1A, 2D6*2, 2D6*2N, 2D6*3, 2D6*4, 2D6*5, 2D6*6, 2D6*7, 2D6*8, 2D6*10, 2D6*12, 2D6*17, or 2D6*35 allele, and the CYP3A4*1A or 3A4*1B allele.

The panel further can include a plurality of dopamine receptor genes (e.g., dopamine receptor genes encoding dopamine receptors D1, D2, D3, D4, D5, and D6), a plurality of serotonin receptor genes (e.g., serotonin receptor genes encoding serotonin receptors 1A, 1B, 1D, 2A, or 2C), a tryptophan hydroxylase gene, and/or a catechol-O-methyl transferase gene. Serotonin receptor gene 2A is particularly useful.

In some embodiments, the panel includes at least 10 cytochrome P450 genes (e.g., genes encoding CYP1A1, 1A2, 1B1, 2A6, 2B6, 2C8, 2C9, 2C18, 2C19, 2D6, 2E1, 3A4, and 3A5). Determining the patient's genotype can include determining if the patient has the CYP1A1*1A, 1A1*2, 1A1*3, or 1A1*4 allele; the 1A2*1A or 1A2*3 allele; the CYP1B1*1, 1B1*2, 1B1*3, 1B1*4, 1B1*11, 1B1*14, 1B1*18, 1B1*19, 1B1*20, or 1B1*25 allele; the CYP2A6*1A, 2A6*1B, 2A6*2, or 2A6*5 allele; the CYP2B6*1, 2B6*2, 2B6*3, 2B6*4, 2B6*5, 2B6*6, or 2B6*7 allele; the CYP2C8*1A, 2C8*1B, 2C8*1C, 2C8*2, 2C8*3, or 2C8*4 allele; the CYP2C9*1, 2C9*2, 2C9*3, or 2C9*5 allele; the CYP2C18*ml or 2C18*m2 allele; the CYP2C19*1A, 2C19*1B, or 2C19*2A allele; the CYP2D6*1A, 2D6*2, 2D6*2N, 2D6*3, 2D6*4, 2D6*5, 2D6*6, 2D6*7, 2D6*8, 2D6*10, 2D6*12, 2D6*17, or 2D6*35 allele; the CYP2E1*1A, 2E1*1C, 2E1*1D, 2E1*2, 2E1*4, 2E1*5, or 2E1*7 allele; the CYP3A4*1A or 3A4*1B allele; and the CYP3A5*1A, 3A5*3, 3A5*5, or 3A5*6 allele.

In some embodiments, the panel of genes contains the CYP2D6, 2C19, 3A4, and 1A2 genes, the serotonin receptor gene, and the serotonin receptor 2A gene. Selecting the psychotropic medication can include correlating genotype of the cytochrome P450 genes with capacity of each cytochrome P450 enzyme encoded by each cytochrome P450 gene to metabolize the psychotropic medication and correlating genotype of the serotonin transporter gene and the serotonin receptor gene with ability of the patient to respond to the psychotropic medication.

In another aspect, the invention features an article of manufacture that includes a substrate. The substrate includes a plurality of discrete regions, wherein each region includes a different population of nucleic acid molecules, wherein the different populations of nucleic acid molecules independently include nucleic acid molecules for detecting the CYP1A1*1A, 1A1*2, 1A1*3, and 1A1*4 alleles; the CYP1A2*1A and 1A2*3 alleles; the CYP2C19*1A, 2C19*1B, and 2C19*2A alleles; the CYP2D6*1A, 2D6*2, 2D6*2N, 2D6*3, 2D6*4, 2D6*5, 2D6*6, 2D6*7, 2D6*8, 2D6*10, 2D6*12, 2D6*17, and 2D6*35 alleles; the CYP3A4*1A and 3A4*11B alleles; the DAT1 40 bp VNTR and 10 repeat alleles; and the 5HTT promoter repeat and exon 2 variable repeat alleles. The population of nucleic acid molecules further can include nucleic acid molecules for detecting the CYP1B1*1, 1B1*2, 1B1*3, 1B1*4, 1B1*11, 1B1*14, 1B1*18, 1B1*19, 1B1*20, and 1B1*25 alleles, the CYP2A6*1A, 2A6*1B, 2A6*2, and 2A6*5 alleles, the CYP2B6-1, 2B6*2, 2B6*3, 2B6*4, 2B6*5, 2B616, and 2B6*7 alleles, the CYP2C8*1A, 2C8*11B, 2C8*1C, 2C8*2, 2C8*3, and 2C8*4 alleles, the CYP2C9*1, 2C9*2, 2C9*3, and 2C9*5 alleles, the CYP2C18*ml and 2C18*m2 alleles, the CYP2C19*1A, 2C19*1B, and 2C19*2A alleles, the CYP2E1*1A, 2E1*1C, 2E1*1D, 2E1*2, 2E1*4, 2E1*5, and 2E1*7 alleles, and the CYP3A5*1A, 3A5*3, 3A5*5, and 3A5*6 alleles. The population further can include nucleic acid molecules for detecting the TPH A218C, A779C, G5806T, A6526G, and (CT)m(CA)n(CT)p alleles.

The invention also features a method of building a database for use in selecting a medication for a patient. The method includes receiving, in a computer system, a plurality of genotypes for a panel of genes; receiving a plurality of medication profiles specified based on the genotypes; and storing the plurality of genotypes and the medication profiles such that each medication profile is associated with one of the genotypes. The at least one medication profile can identify a medication and the medication can be placed in one of multiple categories included in the medication profile. Such categories can be selected from the group consisting of: medications that are safe to use, medications that should be used with caution, medications that should be closely monitored when used, medications that should be avoided, and combinations thereof. The medication profile can identify a universe of possible medications for the patient's genotype.

In another aspect, the invention features a computer program product containing executable instructions that when executed cause a processor to perform operations. The operations can include: receive a plurality of genotypes for a panel of genes; receive a plurality of medication profiles specified based on the genotypes; and store the genotypes and the medication profiles such that each medication profile is associated with one of the genotypes.

The invention also features a method of selecting a medication for a patient. The method includes receiving, in a computer system, a patient's genotype for a panel of genes; identifying, in a database comprising a plurality of medication profiles associated with genotypes, a medication profile that is associated with the patient's genotype; and outputting the identified medication profile in response to receiving the patient's genotype. A user can enter the patient's genotype in the computer system or the patient's genotype can be received directly from equipment used in determining the patient's genotype.

The medication profile can include a ranking of several medications, e.g., based on specific co-factors. The method can include adjusting the ranking before outputting the identified medication profile (e.g., based on receiving a genotypic polymorphism carried by the patient or based on receiving a clinical response relating to the patient). The clinical response can be by a family member of the patient.

In yet another aspect, the invention features a computer program product containing executable instructions that when executed cause a processor to perform operations that include receive a patient's genotype for a panel of genes; identify, in a database including a plurality of medication profiles associated with genotypes, a medication profile that is associated with the patient's genotype; and output the identified medication profile in response to receiving the patient's genotype.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

DESCRIPTION OF THE DRAWINGS

FIG. 2 is a flow chart of a method 200 for building a database for use in selecting a medication for a patient.

FIG. 3 is a flow chart of a method 300 for selecting a medication for a patient.

DETAILED DESCRIPTION

Figure 1:
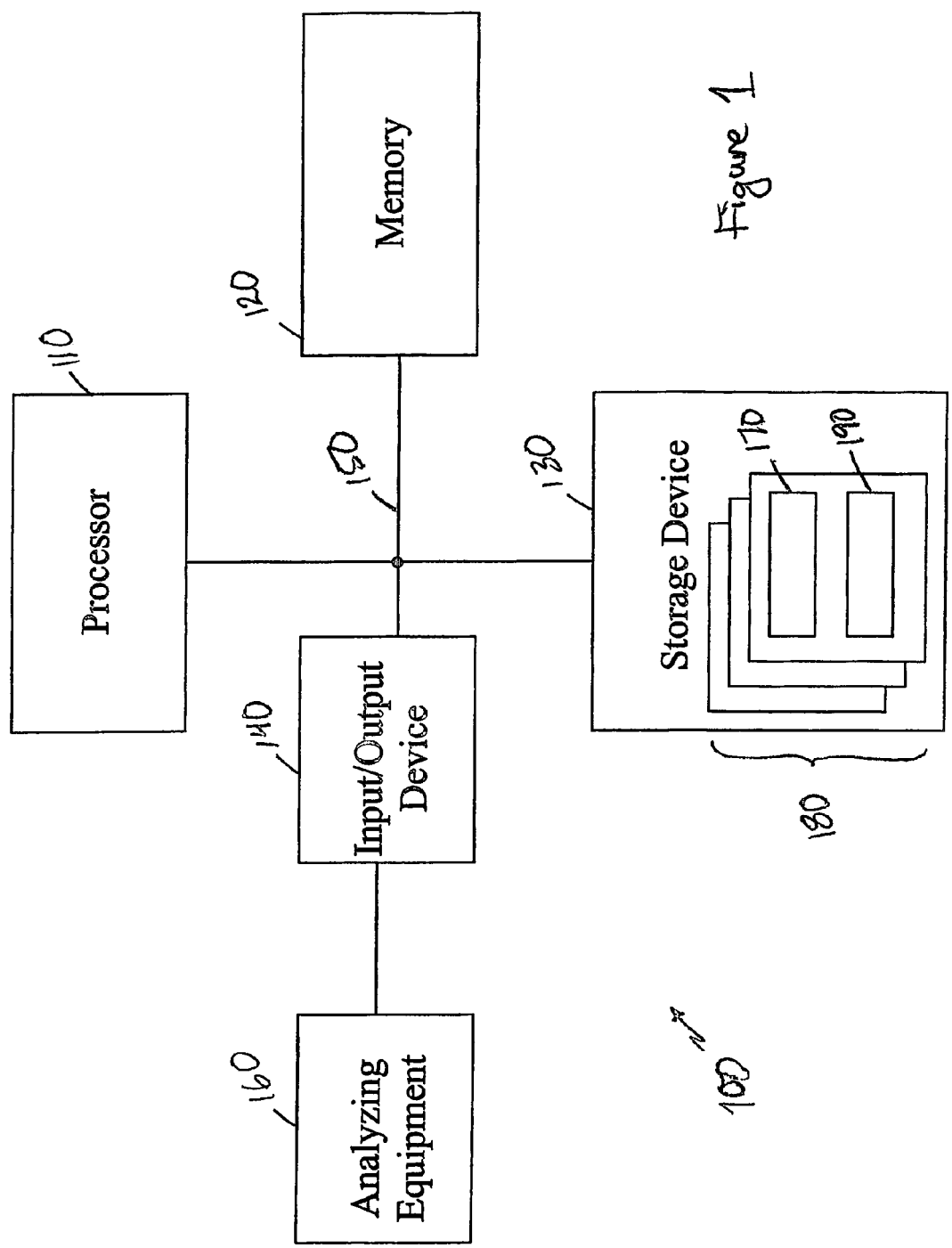
FIG. 1 is a block diagram of a computer system 100, according to one embodiment.

In general, the invention features a method for selecting a medication (e.g., psychotropic medication) for a patient based on the genotype of genes that are useful for medication selection. Genes to be genotyped typically encode products that influence the metabolism of a medication or that are associated with a better treatment response. An algorithm can be used that initially excludes medications based on problematic genotypes of drug metabolizing enzyme genes (e.g., cytochrome P450 genes). A second stage of such an algorithm can begin with a list of potentially appropriate medications (e.g., antidepressants) and result in further classification of optimal treatments based on the genotype of target genes. For example, for antidepressants, further classification of the potential antidepressants can be based on the genotype of the serotonin transporter (5HTTR) and serotonin receptor 2A (HTR2A).

Psychotropic medications include antipsychotics or neuroleptics, antianxiety-sedative agents, antidepressants or mood elevating agents, and mood-stabilizing drugs such as lithium salts or valproic acid. Non-limiting examples of antipsychotics include the tricyclic phenothiazines (e.g., chlorpromazine, triflupromazine, thioridazine, and mesoridazine, fluphenazine, and trifluoperazine), thioxanthenes (e.g., chlorprothixene, clopenthixol, flupenthixol, piflutixol, and thiothixene), and dibenzepines (e.g., loxapine, clozapine, clothiapine, metiapine, zotapine, ICI-204,636, fluperlapine, and olanzapine); butyrophenones such as haloperidol, diphenylbutylpiperidines such as fluspirilene, penfluridol, and pimozide, haloperidol decanoate, and indolones. Non-limiting examples of antianxiety-sedative agents include benzodiazepines such as chlordiazepoxide, diazepam, oxazepam, clorazepate, lorazepam, prazepam, alprazolam, and halazepam). Antidepressants or mood elevating agents include norepinephrine-reuptake inhibitors such as the tertiary amine tricyclics (e.g., amitriptyline, clomipramine, doxepin, and imipramine) and secondary amine tricyclics (e.g., amoxapine, desipramine, maprotiline, protriptyline, and nortriptyline); selective serotonin-reuptake inhibitors (SSRIs) such as fluoxetine, fluvoxamine, paroxetine, sertraline, citalopram, escitalopram, and venlafaxine; atypical antidepressants such as bupropion, nefazodone, and trazodone; noradrenergic and specific serotonergic antidepressants such as mirtazapine; and monoamine oxidase inhibitors such as phenelzine, tranylcypromine, and selegiline.

In certain ethnic groups as many as 10% of the adolescent population have a 2D6 haplotype that is associated with poor metabolism of many antidepressant medications. See Wong et al. (2001) *Ann. Acad. Med. Singapore* 29:401-406. Clinical genomic testing of these individuals has clear implications for their treatment and prognosis. In extreme cases, children who were poor metabolizers and who were not identified have had tragic outcomes. These negative case reports have included a reported death of a nine-year-old boy who was not recognized to be a poor 2D6 metabolizer. The treatment of this child with fluoxetine continued despite the development of multiple symptoms because these symptoms were not recognized as being related to his extremely high serum levels of fluoxetine. Sallee et al. (2000) *J. Child Adol. Psychiatry* 10(1):27-34. While careful clinical surveillance to identify unexpected side effects during the administration of low doses of medication is an alternative clinical strategy to genotyping, genomic testing of a plurality of genes encoding drug metabolizing enzymes (e.g. cytochrome P450 genes) and other target genes (e.g., genes involved in neurotransmission for psychotropic drugs) provides a safe method by which potentially dangerous side effects can be avoided in an affected patient.

Panels of Genes

The method includes obtaining a biological sample from a patient and obtaining the patient's genotype for a panel of genes. Typically, the panel of genes that are genotyped includes at least three cytochrome P450 genes. The cytochrome P450 genes can be selected from the P450 genes listed in Table 1. For example, the at least three cytochrome P450 genes can encode CYP2D6, 1A2, and 2C19. In embodiments for selecting antidepressant medications, the genotype of four cytochrome P450 genes (e.g., genes encoding CYP2D6, 2C19, 3A4, and 1A2) can be obtained. In other embodiments, the genotype of at least 5 cytochrome P450 genes (e.g., genes encoding CYP1A1, 1A2, 2D6, 2C19, and 3A4) can be obtained. In still other embodiments, the genotype of at least 10 cytrochrome P450 genes (e.g., genes encoding CYP1A1, 1A2, 1B1, 2A6, 2B6, 2C8, 2C9, 2C18, 2C19, 2D6, 2E1, 3A4, and 3A5) can be obtained. Alleles for each of these cytochrome P450 genes are set forth in Table 1.

Substrates of CYP2D6 typically are weak bases with the cationic binding site located away from the carbon atom to be oxidized. In particular, substrates of CYP2D6 include amitriptyline, nortriptyline, haloperidol, and desipramine. Some individuals have altered CYP2D6 gene sequences that result in synthesis of enzymes devoid of catalytic activity or in enzymes with diminished catalytic activity. These individuals metabolize SSRIs and tricyclic antidepressants (TCAs) poorly. Duplication of the functional CYP2D6 gene also has been observed and results in ultrarapid metabolism of SSRIs and other drugs. Individuals without inactivating polymorphisms, deletions, or duplications have the phenotype of an extensive drug metabolizer and are designated as CYP2D6*1. The CYP2D6*2 allele has decreased enzymatic activity resulting from amino acid substitutions. The CYP2D6*3 and *4 alleles account for nearly 70% of the total deficiencies that result in the poor metabolizer phenotype. The polymorphism responsible for CYP2D6*3 (2549A>del) produces a frame-shift in the mRNA. A polymorphism involved with the CYP2D6*4 allele (1846G>A) disrupts mRNA splicing. These changes produce truncated forms of CYP2D6 devoid of catalytic activity. Other poor metabolizers are CYP2D6*5, *10, and *17. CYP2D6*5 is due to complete gene deletion. The polymorphisms in CYP2D6*10 and *17 produce amino acid substitutions in the CYP2D6 enzyme which have decreased enzyme activity. All of these polymorphisms are autosomal recessive. Consequently, only individuals who are homozygous or who are compound heterozygous for these polymorphisms are poor metabolizers. Individuals who are heterozygous, with one normal gene and one polymorphic gene, will have metabolism intermediate between the extensive (normal) and poor metabolizers.

CYP1A2 metabolizes many aromatic and heterocyclic amines including clozapine and imipramine. The CYP1A2 *1F allele can result in a product with higher inducibility or increased activity. See Sachse et al. (1999) *Br. J. Clin. Pharmacol.* 47: 445-449. CYP2C19 also metabolizes many substrates including imipramine, citalopram, and diazepam. The CYP2C19*2A, *2B, *3, *4, *5A, *5B, *6, *7, and *8 alleles encode products with little or no activity. See Ibeanu et al. (1999) *J. Pharmacol. Exp. Ther.* 290: 635-640.

CYP1A1 can be associated with toxic or allergic reactions by extrahepatic generation of reactive metabolites. CYP3A4 metabolizes a variety of substrates including alprazolam. CYP1B1 can be associated with toxic or allergic reactions by extrahepatic generation of reactive metabolites and also metabolizes steroid hormones (e.g., 17β-estradiol). Substrates for CYP2A6 and CYP2B6 include valproic acid and bupropion, respectively. Substrates for CYP2C9 include Tylenol and antabuse (disulfiram). Substrates for CYP2E1 include phenytoin and carbamazepine. Decreases in activity in one or more of the cytochrome P450 enzymes can impact one or more of the other cytochrome P450 enzymes.

TABLE 1

Cytochrome P450 Genes

| Cytochrome P450Gene | Allele | Polymorphism |
|---|---|---|
| 1A1 | *1A | None |
|  | *2 | A2455G |
|  | *3 | T3205C |
|  | *4 | C2453A |
| 1A2 | *1A | None |
|  | *1F | −164C > A |
|  | *3 | G1042A |
| 1B1 | *1 | None |
|  | *2 | R48G |
|  | *3 | L432V |
|  | *4 | N453S |
|  | *11 | V57C |
|  | *14 | E281X |
|  | *18 | G365W |
|  | *19 | P379L |
|  | *20 | E387K |
|  | *25 | R469W |
| 2A6 | *1A | None |
|  | *1B | CYP2A7 translocated to 3'-end |
|  | *2 | T479A |
|  | *5 | *1B + G6440T |
| 2B6 | *1 |  |
|  | *2 | R22C |
|  | *3 | S259C |
|  | *4 | K262R |
|  | *5 | R487C |
|  | *6 | Q172H; K262R |
|  | *7 | Q172H; K262R; R487C |
| 2C8 | *1A | None |
|  | *1B | −271C > A |
|  | *1C | −370T > G |
|  | *2 | I269F |
|  | *3 | R139K; K399R |
|  | *4 | I264M |
| 2C9 | *1 | None |
|  | *2 | R144C |
|  | *3 | I359L |
|  | *5 | D360E |
| 2C18 | m1 | T204A |
|  | m2 | A460T |
| 2C19 | *1A | None |
|  | *1B | I331V |
|  | *2A | Splicing defect |
|  | *2B | Splicing defect; E92D |
|  | *3 | New stop codon 636G > A |
|  | *4 | GTG initiation codon, 1A > G |
|  | *5(A, B) | 1297C > T, amino acid change (R433W) |
|  | *6 | 395G > A, amino acid change (R132Q) |
|  | *7 | IVS5 + 2T > A, splicing defect |
|  | *8 | 358T > C, amino acid change (W120R) |
| 2D6 | *1A | None |
|  | *2 | G1661C, C2850T |
|  | *2N | Gene duplication |
|  | *3 | A2549 deletion |
|  | *4 | G1846A |
|  | *5 | Gene deletion |

TABLE 1-continued

Cytochrome P450 Genes

| Cytochrome P450Gene | Allele | Polymorphism |
|---|---|---|
| | *6 | T1707 deletion |
| | *7 | A2935C |
| | *8 | G1758T |
| | *10 | C100T |
| | *12 | G124A |
| | *17 | C1023T, C2850T |
| | *35 | G31A |
| 2E1 | *1A | None |
| | *1C, *1D | (6 or 8 bp repeats) |
| | *2 | G1132A |
| | *4 | G476A |
| | *5 | G(−1293)C |
| | *5 | C(−1053)T |
| | *7 | T(−333)A |
| | *7 | G(−71)T |
| | *7 | A(−353)G |
| 3A4 | *1A | None |
| | *1B | A(−392)G |
| | *2 | Amino acid change (S222P) |
| | *5 | Amino acid change (P218R) |
| | *6 | Frameshift, 831 ins A |
| | *12 | Amino acid change (L373F) |
| | *13 | Amino acid change (P416L) |
| | *15A | Amino acid change (R162Q) |
| | *17 | Amino acid change (F189S, decreased) |
| | *18A | Amino acid change (L293P, increased) |
| 3A5 | *1A | None |
| | *3 | A6986G |
| | *5 | T12952C |
| | *6 | G14960A |

Typically, to select a medication, the genotype of other target genes also is obtained in addition to the genotype of the genes encoding drug-metabolizing enzymes. Target genes can encode products that relate to the ability of the patient to respond to a particular class of medication. For example, to select an antidepressant, the target genes can be the serotonin transporter gene and serotonin receptor 2A gene. To select an antipsychotic, the target gene can be a dopamine transporter gene.

Table 2 sets forth the alleles for target genes that can be genotyped in addition to the genes encoding drug-metabolizing enzymes. For example, the panel of genes to be genotyped can include one or more dopamine receptor genes (e.g., genes encoding dopamine receptors D1, D2, D3, D4, D5, and/or D6), a dopamine transporter gene, one or more serotonin receptor genes (e.g., genes encoding serotonin receptors 1A, 1B, 1D, 2A, or 2C), a catechol-O-methyl transferase (COMT) gene, or a tryptophan hydroxylase gene. In one embodiment, a COMT gene and a tryptophan hydroxylase gene are included on the panel with cytochrome P450 genes. In other embodiments, one or more dopamine receptor genes, one or more serotonin receptor genes, a COMT gene, and a tryptophan hydroxylase gene are assessed in combination with the cytochrome P450 genes.

TABLE 2

| Gene | Symbol | Polymorphism |
|---|---|---|
| Dopamine Transporter | DAT1, SLC6A3 | 40 bp VNTR |
| | | 10 repeat allele |
| | | G710A, Q237R |
| | | C124T, L42F |
| Dopamine Receptor D1 | DRD1 | DRD1 B2 |
| | | T244G |
| | | C179T |
| | | G127A |
| | | T11G |
| | | C81T |
| | | T595G, S199A |
| | | G150T, R50S |
| | | C110G, T37R |
| | | A109C, T37P |
| Dopamine Receptor D2 | DRD2 | TaqI A |
| | | A1051G, T35A |
| | | C932G, S311C |
| | | C928, P310S |
| | | G460A, V154I |
| Dopamine Receptor D3 | DRD3 | BalI in exon I |
| | | MspI |
| | | DRD3 1 |
| | | Gly/Ser (allele 2) |
| | | A25G, S9G |
| Dopamine Receptor D4 | DRD4 | 48 repeat in exon 3 |
| | | 7 repeat allele |
| | | 12/13 bp insertion/deletion |
| | | T581G, V194G |
| | | C841G, P281A |
| Dopamine Receptor D5 | DRD5 | T978C |
| | | L88F |
| | | A889C, T297P |
| | | G1252A, V418I |
| | | G181A, V61M |
| | | G185C, C62S |
| | | T263G, R88L |
| | | G1354A, W455 |
| Tryptophan Hydroxylase | TPH | A218C |
| | | A779C |
| | | G-5806T |
| | | A-6526G |
| | | $(CT)_m(CA)_n(CT)_p$ allele 194 in 3' UTR, 5657 bp distant from exon 11 |
| Serotonin Transporter | 5-HTTR | Promoter repeat (44 bp insertion (L)/deletion(S) (L = Long form; S = Short form) |
| | | Exon 2 variable repeat |
| | | A1815C |
| | | G603C |
| | | G167C |
| Serotonin Receptor 1A | HTR1A | RsaI |
| | | G815A, G272D |
| | | G656T, R219L |
| | | C548T, P551L |
| | | A82G, I28V |
| | | G64A, G22S |
| | | C47T, P16L |
| Serotonin Receptor 1B | HTR1B | G861C |
| | | G861C, V287V |
| | | T371G, F124C |
| | | T655C, F219L |
| | | A1099G, I367V |
| | | G1120A, E374K |
| Serotonin Receptor 1D | HTR1D | G506T |
| | | C173T |
| | | C794T, S265L |
| Serotonin Receptor 2A | HTR2A | C74A |
| | | T102C |
| | | T516C |
| | | C1340T |
| | | C1354T |
| Serotonin Receptor 2C | HTR2C | G796C |
| | | C10G, L4V |
| | | G68C, C23S |
| Catechol-o-methyltransferase | COMT | G158A (Also known as Val/Met) |
| | | G214T |
| | | A72S |
| | | G101C |
| | | C34S |
| | | G473A |

For example, to select an antidepressant, the genotype of four cytochrome P450 genes (e.g., genes encoding 2D6, 2C19, 3A4, and 1A2), the serotonin transporter (5HTTR) gene, and serotonin receptor 2A (HTR2A) gene can be assessed in a patient. In particular, it can be determined if the patient contains the CYP2D6 *2, *3, *4, *10, *17, or *5 del allele, the CYP2C19 *2(A,B), *3, *4, *5 (A,B), *6, *7, *8 alleles, the CYP3A4 *1B, *2, *5, *6, *12, *13, *15A, *17, or *18A alleles, the CYP1A2*1F allele, the short or long form of the serotonin transporter gene, and the HTR2A T102C polymorphism. Each of these genes influences the metabolism of at least one antidepressant medication or is associated with a better treatment response. As described herein, an algorithm has been created based on a set of six rules relating to the genotype of these six genes. Based on this algorithm, medication profiles are provided for a given patient based on the patient's genotype, allowing a clinician to select an acceptable antidepressant without the trial and error of determining if the patient will respond or tolerate a particular antidepressant.

Determining Genotype

Genomic DNA generally is used to determine genotype, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the genotyping. For example, polymerase chain reaction (PCR) techniques can be used to obtain amplification products from the patient. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis (1992) *Genetic Engineering News* 12(9):1; Guatelli et al. (1990) *Proc. Natl. Acad. Sci. USA* 87:1874-1878; and Weiss (1991) *Science* 254:1292-1293.

Primers typically are single-stranded or double-stranded oligonucleotides that are 10 to 50 nucleotides in length, and when combined with mammalian genomic DNA and subjected to PCR conditions, is capable of being extended to produce a nucleic acid product corresponding to a region of interest within a gene. Typically, PCR products are at least 30 nucleotides in length (e.g., 30, 35, 50, 100, 250, 500, 1000, 1500, or 2000 or more nucleotides in length). Primers such as those listed in Table 7 are particularly useful for producing PCR products for the genes encoding the dopamine transporter, dopamine receptors, tryptophan hydroxylase, serotonin transporter, serotonin receptors, and COMT. Specific regions of mammalian DNA can be amplified (i.e., replicated such that multiple exact copies are produced) when a pair of oligonucleotide primers is used in the same PCR reaction, wherein one primer contains a nucleotide sequence from the coding strand of a nucleic acid and the other primer contains a nucleotide sequence from the non-coding strand of the nucleic acid. The "coding strand" of a nucleic acid is the nontranscribed strand, which has the same nucleotide sequence as the specified RNA transcript (with the exception that the RNA transcript contains uracil in place of thymidine residues), while the "non-coding strand" of a nucleic acid is the strand that serves as the template for transcription.

A single PCR reaction mixture may contain one pair of oligonucleotide primers. Alternatively, a single reaction mixture may contain a plurality of oligonucleotide primer pairs, in which case multiple PCR products can be generated (e.g., 5, 10, 15, or 20 primer pairs). Each primer pair can amplify, for example, one exon or a portion of one exon. Intron sequences also can be amplified.

Exons or introns of a gene of interest can be amplified then directly sequenced. Dye primer sequencing can be used to increase the accuracy of detecting heterozygous samples. Alternatively, one or more of the techniques described below can be used to determine genotype.

For example, allele specific hybridization can be used to detect sequence variants, including complete haplotypes of a mammal. See, Stoneking et al., 1991, *Am. J. Hum. Genet.* 48:370-382; and Prince et al., 2001, *Genome Res.*, 11(1):152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For ensample, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate (e.g., in discrete regions).

Allele-specific restriction digests can be performed in the following manner. For nucleotide sequence variants that introduce a restriction site, restriction digest with the particular restriction enzyme can differentiate the alleles. For sequence variants that do not alter a common restriction site, mutagenic primers can be designed that introduce a restriction site when the variant allele is present or when the wild type allele is present. A portion of the nucleic acid of interest can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of a gene of interest can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Kits also are available commercially to detect many of the cytochrome P450 variants. For example, TAG-IT™ kits are available from Tm Biosciences Corporation (Toronto, Ontario).

Selecting Medications

After the genotype is determined for each gene on the panel, the medication can be selected. Typically, selecting includes correlating genotype of the cytochrome P450 genes with capacity of each cytochrome P450 enzyme encoded by each cytochrome P450 gene to metabolize the medication. The genotype of other target genes on the panel, e.g., the serotonin transporter and/or dopamine transporter genes, can be correlated with the ability of the patient to respond to the medication.

An algorithm can be used to select the most appropriate medications for an individual patient. The design of the algorithm requires the initial identification of the phenotype, which provides a preliminary identification of the universe of possible medications. At the next step of the algorithm, the results of the target gene analyses can be sequentially entered. The potential list of appropriate medications can be subsequently rank-ordered based on specific co-factors in the algorithmic equation, which assign a positive, negative, or neutral probability score to each of the identified medications in the originally identified set of possible choices. This process adjusts the rank ordering based on the genotypic polymorphism carried by the patient. At the next entry point in the algorithmic equation, the results of the CYP gene analyses can be introduced. This algorithmic analysis is designed to place the medications in three categories: 1) medications that are acceptable for use, i.e., the medication has a high probability of normal metabolism within an individual having a particular genotype, 2) medications that can be used with caution (e.g., medication may require some dosing adjustment based on atypical metabolism); and 3) medications that should be avoided or used with caution and monitoring, e.g., due to potential difficulties in dosing. At this point in the selection process, data related to the medication response of first- and second-degree relatives of the patient can be entered into the algorithmic equation, which pertains to the medication selection of drugs in the first category that has been identified. An adjustment of the rank-ordered, appropriate medications then can be calculated based on clinical responses by family members.

The selection of an appropriate medication further can be enhanced by including both target data and data related to drug metabolism. This can determine the impact of the CYP products on the clinical response of a particular patient. For example, inclusion of target data and data related to drug metabolism provides the amount of available drug, the ability of the patient to utilize the drug, and information about the quality of the receptor target of the drug, providing a rational approach to selection of medication.

An example of this process would be the selection of an appropriate antidepressant for a given patient. Once the phenotype of depression is established, the initial universe of antidepressant medications is identified. For example, citalopram, fluvoxamine, bupropion, escitalopram, sertraline, mirtazapine, fluoxetine, venlafaxine, amitriptyline, imipramine, paroxetine, and nortriptyline can be the initial universe of antidepressant medications. It is understood that this initial universe of medications can change as additional antidepressants become available or as additional pharmacogenomic data are available. Subsequently, the data from the target genotyping is entered. If during the first components of the algorithm, it is revealed that the genotype reflects poor metabolism for 2D6 and normal metabolism for 1A2, the rank ordering of medication would be to identify fluvoxamine and buproprion as medications that are likely to be both effective and appropriately managed at recommended doses. At the next stage of the algorithm, if an individual is homozygous for the long form of the serotonin transporter gene, fluvoxamine would be confirmed as being acceptable for use. Output from the algorithm then can be integrated with historical data. For example, if a family member had responded well to fluvoxamine, this would confirm that the medication is acceptable for use, or, if a first or second degree relative had a problematic response to this medication, an alternative could be chosen.

Computer Systems

Techniques described herein can be implemented in a computer system having a processor that executes specific instructions in a computer program. The computer system may be arranged to output a medication profile based on receiving a patient's genotype. Particularly, the computer program may include instructions for the system to select the most appropriate medication (e.g., a psychotropic medication) for an individual patient.

The following are examples of features that may be included in a system. The computer program may be configured such that the computer system can identify the phenotype based on received data and provide a preliminary identification of the universe of possible medications. The system may be able to rank-order the identified medications based on specific co-factors in the algorithmic equation. The system may be able to adjust the rank ordering based on the genotypic polymorphism(s) carried by the patient. The system may be able to adjust the rank ordering based on clinical responses, such as by family members of the patient.

FIG. 1 is a block diagram of a computer system 100 that can be used in the operations described above, according to one embodiment. The system 100 includes a processor 110, a memory 120, a storage device 130 and an input/output device 140. Each of the components 110, 120, 130 and 140 are interconnected using a system bus 150. The system may include analyzing equipment 160 for determining the patient's genotype.

The processor 110 is capable of processing instructions for execution within the system 100. In one embodiment, the processor 110 is a single-threaded processor. In another embodiment, the processor 110 is a multi-threaded processor. The processor 110 is capable of processing instructions stored in the memory 120 or on the storage device 130, including for receiving or sending information through the input/output device 140.

The memory 120 stores information within the system 100. In one embodiment, the memory 120 is a computer-readable medium. In one embodiment, the memory 120 is a volatile memory unit. In another embodiment, the memory 120 is a non-volatile memory unit.

The storage device 130 is capable of providing mass storage for the system 100. In one embodiment, the storage device 130 is a computer-readable medium. In various different embodiments, the storage device 130 may be a floppy disk device, a hard disk device, an optical disk device, or a tape device.

The input/output device 140 provides input/output operations for the system 100. In one embodiment, the input/output device 140 includes a keyboard and/or pointing device. In one embodiment, the input/output device 140 includes a display unit for displaying graphical user interfaces.

The system 100 can be used to build a database. FIG. 2 shows a flow chart of a method 200 for building a database for use in selecting a medication for a patient. Preferably, the method 200 is performed in the system 100. For example, a computer program product can include instructions that cause the processor 110 to perform the steps of the method 200. The method 200 includes the following steps.

Receiving, in step 210, a plurality of genotypes 170 for a panel of genes. A computer program in the system 100 may include instructions for presenting a suitable graphical user interface on input/output device 140, and the graphical user interface may prompt the user to enter the genotypes 170 using the input/output device 140, such as a keyboard.

Receiving, in step 220, a plurality of medication profiles 180. The medication profiles 180 are specified based on the genotypes 170. The user may enter the medication profiles 180 using the input/output device 140, such as a keyboard. For example, the medication profile 180 may include information 190 regarding at least one medication.

Storing, in step 230, the received genotypes 170 and the medication profiles 180 such that each medication profile 180 is associated with one of the genotypes 170. The system 100 may store the medication profiles 180 and the genotypes 170 in the storage device 130. For example, when the storing is complete, the system 100 can identity a particular one of the medication profiles 180 that is associated with a specific genotype 170. Having identified the medication profile 180, the system 100 can access the information 190 contained within the identified medication profile 180, as will be described in the following example.

The system 100 may be used for selecting a medication. FIG. 3 shows a flow chart of a method 300 of selecting a medication for a patient. Preferably, the method 300 is performed in the system 100. For example, a computer program product can include instructions that cause the processor 110 to perform the steps of the method 300. The method 300 includes the following steps.

Receiving, in step 310, a patient's genotype for a panel of genes. The genotype may be entered by a user via input/output device 140. For example, the user may obtain the patient's genotype for a panel of genes using the analyzing equipment 160 (which may or may not be connected to the system 100). The user may type the patient's genotype on input/output device 140, such as a keyboard, for receipt by the system 100.

The genotype may be received directly from the analyzing equipment 160. For example, analyzing equipment 160 may include a processor and suitable software such that it can communicate over a network. The system 100 may be connected to the analyzing equipment 160 through input/output device 140, such as a network adapter, and directly receive the patient's genotype.

Identifying, in step 320, one of the medication profiles 180 that is associated with the patient's genotype. For example, the system 100 may perform a database search in the storage device 130. Particularly, the system 100 may access the genotype 170 for individual medication profiles 180 until a match is found. Optional step 325 will be described below.

Outputting, in step 330, the identified medication profile 180 in response to receiving the patient's genotype. The system may output the identified medication profile 180 through input/output device 140. For example, the identified medication profile may be printed or displayed in a suitable graphical user interface on a display device. As another example, the system 100 may transmit the identified medication profile over a network, such as a local area network or the Internet, to which the input/output device 140 is connected.

The medication profiles 180 can be created such that there is flexibility in how the system 100 outputs them. For example, the information 190 in one or more of the medication profiles 180 may include a ranking of several medications. The program may include instructions for applying rules to the received patient's genotype and adjust the ranking accordingly. In such implementations, the method 300 may include optional step 325 of adjusting the ranking before outputting the identified medication profile. For example, the system 100 may receive a genotypic polymorphism carried by the patient (optionally in the same way the patient's genotype was received) and adjust the ranking accordingly in step 325. As another example, step 325 may involve adjusting the ranking based on a clinical response. The clinical response may be received by the system 100 in the same way as the patient's genotype. For example, the ranking can be adjusted based on a clinical response by a member of the patient's family.

The medication profiles 180 may be updated as necessary. For example, the introduction of a new medication on the market may prompt a revision of one or more existing medication profiles. A new medication may also be the basis for creating a new medication profile. The adjustment or creation of medication profiles may be done substantially as described above.

The medication profiles 180 may be used for medication selection in the same system where they were created, or in a different system. That is, the system 100 may first be used for building a database of the medication profiles 180, and the system 100 may thereafter be used to select a medication profile for the genotype of a specific patient. As another example, one or more medication profiles 180 may be transmitted within a computer readable medium such as a global computer network for remote processing according to the invention.

Articles of Manufacture

In one embodiment, the article of manufacture is a composition containing oligonucleotide primers. Typically, such a composition will contain a first oligonucleotide primer and a second oligonucleotide primer, each 10 to 50 nucleotides in length, which can be combined with genomic DNA from a mammal and subjected to PCR conditions, to produce a nucleic acid product that corresponds to a region of interest within a target gene. A composition also may contain buffers and other reagents necessary for PCR (e.g., DNA polymerase or nucleotides). Furthermore, a composition may contain one or more additional pairs of oligonucleotide primers (e.g., 5, 10, 15, or 20 primer pairs), such that multiple nucleic acid products can be generated.

In other embodiments, articles of manufacture include populations of nucleic acid molecules immobilized on a substrate. Suitable substrates provide a base for the immobilization of the nucleic acids, and in some embodiments, allow immobilization of nucleic acids into discrete regions. In embodiments in which the substrate includes a plurality of discrete regions, different populations of isolated nucleic acids can be immobilized in each discrete region. The different populations of nucleic acid molecules independently can include nucleic acid molecules for detecting one or more of the alleles set forth in Tables 1 and 2.

Suitable substrates can be of any shape or form and can be constructed from, for example, glass, silicon, metal, plastic, cellulose or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules typically are about 20 nucleotides in length, but can vary from about 10 nucleotides to about 1000 or more nucleotides in length.

The invention will be further described in the following examples, which do not limit the scope of the invention described in the claims.

EXAMPLES

Example 1

CYP450 Genotype of Patients

This experiment highlights the results of an assessment of adolescents with atypical responses to selective serotonin reuptake inhibitors. The following CYP2D6 alleles that produce deficiencies were detected: *2 (1661G>C and 2850C>T), *3 (2549A>del), *4 (1661G>C and 1846G>A), *10 (100C>T, 1661G>C and 1846G), *17 (1023C>T and 2850C>T). Deletion of CYP2D6 (*5 del) was detected by electrophoresis following PCR amplification. Tandem duplication of the CYP2D6 gene was detected by amplification of a duplication-specific sequence with detection following electrophoresis.

Genomic DNA was amplified by the polymerase chain reaction in an Applied Biosystems Thermal Cycler using the primers listed below. The lower case letters "f" and "r" imply the direction of synthesis ("f" indicates a forward/sense synthesis reaction and "r" indicates a reverse/antisense synthesis reaction). The amplified DNA was hybridized with oligonucleotide probes (described below) specific for the normal and polymorphic variants and detected using the Nanogen Molecular Biology Workstation. The oligonucleotide probes were fluorescently labeled (e.g., CY3 or CY5).

PreNest Oligonucleotides (Primary Amplification)

Amplification Primers:

```
CYP2D6 Prenest B F
5'-CCA GAA GGC TTT GCA GGC TTC      (Bases 1281-1302,
A-3'                                 SEQ ID NO: 1)

CYP2D6 Prenest B R
5'-ACT GAG CCC TGG GAG GTA GGT      (Bases 6357-6378,
A-3'                                 SEQ ID NO: 2)
```

Nest Oligonucleotides (Secondary Amplification)

CYP2D6 (C100T)

Amplification Primers:

```
CYP2D6 (100)B f
5'GGC CTA CCC TGG GTA AGG GCC       (Bases 1579-1594,
TGG AGC AGG A-3'                     SEQ ID NO: 3)

CYP2D6 (100)B r
5'-/5Bio/CCT GGT CGA AGC AGT AT-    (Bases 2394-2411,
3'                                   SEQ ID NO: 4)
```

Probes and Stabilizers

```
CYP2D6 C100T wild type
5'-/5Cy3/GCA CGC TAC C-3'           (Bases 1700-1710,
                                     SEQ ID NO: 5)

CYP2D6 C100T polymorphism
5'-/5Cy5/GCA CGC TAC T-3'           (Bases 1700-1710,
                                     SEQ ID NO: 6)

CYP2D6 C100T stabilizer
5'CAC CAG GCC CCC TGC CAC TG-3'     (Bases 1711-1731,
                                     SEQ ID NO: 7)
```

CYP2D6 (C1023T)

Amplification Primers:

```
CYP2D6 (1023)B f
5'-CCT GCT CAC TCC TGG TAG CC-3'    (Bases 2394-2413,
                                     SEQ ID NO: 8)

CYP2D6(1023) B r
5'-/5Bio/CTG TTT CAT GTC CAC GAC    (Bases 2760-2779,
C-3'                                 SEQ ID NO: 9)
```

Probes and Stabilizers

```
CYP2D6 (1023) wild type
5'-/5Cy3/TGC CCA TCA C-3'        (Bases 2632-2642,
                                 SEQ ID NO: 10)

CYP2D6 (1023) polymorphism
5'-/5Cy3/TGC CCA TCA T-3'        (Bases 2632-2642,
                                 SEQ ID NO: 11)

CYP2D6 (1023) stabilizer
5'CCA GAT CCT GGG TTT CGG GCC    (Bases 2643-2667,
GCG-3'                           SEQ ID NO: 12)
```

CYP2D6 (G1661C and G1846A)

Note: There are 2 polymorphisms on this amplicon.

Amplification Primers

```
CYP2D6 (1661, 1846)B f
5'-CAG AGG CGC TTC TCC G-3'      (Bases 3266-3282,
                                 SEQ ID NO: 13)

CYP2D6 (1661, 1846)B r
5'-/5Bio/CTC GGT CTC TCG CTC CGC (Bases 3630-3650,
AC-3'                            SEQ ID NO: 14)
```

Probes and Stabilizers

```
CYP2D6(1661) wild type
5'-/5Cy3/CTT CTC CGT G-3'        (Bases 3266-3276,
                                 SEQ ID NO: 15)

CYP2D6(1661) polymorphism
5'-/5Cy3/CTT CTC CGT C-3'        (Bases 3266-3276,
                                 SEQ ID NO: 16)

CYP2D6(1661) stabilizer
5'-TCC ACC TTG CGC AAC TTG GGC   (Bases 3277-3303,
CTG GG-3'                        SEQ ID NO: 17)

CYP2D6(1846) wild type
5'-/5Cy3/CCA CCC CCA G-3'        (Bases 3460-3470,
                                 SEQ ID NO: 18)

CYP2D6(1846) polymorphism
5'-/5Cy3/CCA CCC CCA A-3'        (Bases 3460-3470,
                                 SEQ ID NO: 19)

CYP2D6(1846) stabilizer
5'-GAC GCC CCT TTC GCC CCA ACG-  (Bases 3471-3492,
3'                               SEQ ID NO: 20)
```

CYP2D6 (A2549del and C2850T)

Amplification Primers:

```
CYP2D6 (A2549del and C2850T)B f
5'-TGA GAC TTG TCC AGG TGA AC-3' (Bases 4001-4022,
                                 SEQ ID NO: 21)

CYP2D6 (A2549del and C2850T)B r
5'-/5Bio/CCC AGA TGG GCT CAC GCT (Bases 4558-4578,
GC-3'                            SEQ ID NO: 22)
```

Probes and Stabilizers

```
CYP2D6 (2549) wild type
5'-/5Cy3/ACT GAG CAC A-3'        (Bases 4161-4171,
                                 SEQ ID NO: 23)

CYP2D6 (2549) polymorphism
5'-/5Cy3/ACT GAG CAC G-3'        (Bases 4161-4171,
                                 SEQ ID NO: 24)

CYP2D6 (2549) stabilizer
5'-GGA TGA CCT GGG ACC CAG CCC   (Bases 4172-4199,
AGC C3'                          SEQ ID NO: 25)

CYP2D6 (2850) wild type
5'-/5Cy3/GAG AAC CTG C-3'        (Bases 4462-4472,
                                 SEQ ID NO: 26)

CYP2D6 (2850) polymorphism
5'-/5Cy3/GAG AAC CTG T-3'        (Bases 4462-4472,
                                 SEQ ID NO: 27)

CYP2D6 (2850) stabilizer
5'-GCA TAG TGG TGG CTG ACC TGT   (Bases 4473-4500,
TCT CTG-3'                       SEQ ID NO: 28)
```

PCR Amplification.

A. PreNest (Initial Amplification):

CYP2D6 PreNest B

The initial PreNest PCR for the CYP2D6(C1661G), CYP2D6 (G1846A), CYP2D6(A2549Del), CYP2D6 (C100T), CYP2D6(C2850T), and CYP2D6 (C1023T) polymorphisms was performed with the following reagents per sample: 0.6 μL 25 μM PreNest B F, 0.6 μL 25 μM PreNestB R, 2.5 μL 10 mM dNTP's, 39.55 μL dH$_2$O, 5.0 μL Expand Buffer 3 (Roche), 0.75 μL Expand Enzyme Mix (Roche), and 1.0 μl genomic DNA in a total volume of 50 μL. PCR was performed by holding at 94° C. for 2 minutes then 30 cycles of denaturation at 94° C. for 30 seconds, annealing at 67° C. for 30 seconds, and extension at 68° C. for 7 minutes, followed by a final extension at 72° C. for 10 minutes. The expected PCR product was ≈4.8-5Kb.

All subsequent PCR's were performed using the PreNest B product as the template for the amplification.

CYP2D6(100) B

The (C100T) nested PCR was performed using 1 μl of the initial PreNest B amplicon as template. The product of this PCR was used to detect the CYP2D6(C100T) mutation and uses the following reagents (25 μL total volume): 1.0 μl 25 μM CYP2D6(100) B f, 1.0 μl 25 μM CYP2D6(100) B r, 12.5 μl Qiagen Hot Start Master Mix, and 9.5 μl dH$_2$O. PCR was performed by holding at 95° C. for 15 minutes, then 30 cycles of denaturation at 95° C. for 30 sec, annealing at 57° C. for 30 sec, and extension at 72° C. for 1 min, followed by a final extension at 72° C. for 7 min.

CYP2D6(1023)B

A (C1023T) nested PCR was performed using 1 μl of PreNest B product as template. The product of this PCR was used to detect the CYP2D6 (C1023T) mutation and uses the following reagents (25 μL total volume): 1.0 μl 25 μM CYP2D6 (1023) B f, 1.0 μl 25 μM CYP2D6 (1023)B r, 12.5 μl Amplitaq Gold Master Mix, and 9.5 μl dH$_2$O. PCR was performed by holding at 95° C. for 10 min, then 30 cycles of denaturation at 95° C. for 30 sec, annealing at 59° C. for 30 sec, and extension at 72° C. for 1 min, followed by a final extension at 72° C. for 7 min.

CYP2D6(C1661G and G1846A) B

The (C1661 G and G1846A) nested PCR was performed using 1 μl of PreNest B product as template. The product of this PCR was used to detect the CYP2D6 (C1661G) and CYP2D6 (G1846A) mutations and uses the following reagents (25 μL total volume): 1.0 μl 25 μM CYP2D6 (1661, 1846)B f, 1.0 μl 25 μM CYP2D6 (1661,1846)B r, 12.5 μl 2× Amplitaq Gold Master Mix, and 9.5 μl dH$_2$O. PCR was performed by holding at 95° C. for 10 min, then 30 cycles of denaturation at 95° C. for 30 sec, annealing at 63° C. for 30 sec, and extension at 72° C. for 1 min, followed by a final extension at 72° C. for 7 min.

CYP2D6 (A2549Del and CYP2D6C2850T)B

The (A2549Del and C2850T) nested PCR was performed using 1 μl of PreNest B product as template. The product of this PCR was used to detect the CYP2D6 (A2549Del) and CYP2D6 (C2850T) mutations and uses the following reagents (25 μL total volume): 1.0 μl 25 μM CYP2D6 (2549, 2850)B f, 1.0 μl 25 μM CYP2D6 (2549,2850)B r, 12.5 μl 2× Amplitaq Gold Master Mix, and 9.5 μl dH$_2$O. PCR was performed by holding at 95° C. for 10 min, then 30 cycles of denaturation at 95° C. for 30 sec, annealing at 57° C. for 30 sec, and extension at 72° C. for 1 min, followed by a final extension at 72° C. for 10 min.

Polymorphisms were detected using the Nanogen Molecular Biology Workstation according to the Nanogens User's manual. Samples were desalted on Millipore desalting plates. In a 1.5 ml centrifuge tube, the following reagents were added: 2.0 μl of wild type probe, 2.0 μl of polymorphism probe, 2.0 μl of stabilizer, and 44 μl high salt buffer. Each assay had probes and stabilizers that were labeled and specific to it. The reagents were vortexed, spun briefly, and dispensed over the Nanochip array for 5 minutes and placed in a dark container. The chips were read with a trending method from 24° C. to 50° C., with readings every two degrees. It was confirmed that the fluorescent probe hybridized at 24° C. and that all probes had de-hybridized at 50° C. If the relative fluorescence units (RFUs) were above 80 on any chip at 50° C., the chips were stripped in 200 μl of 1.0 M NaOH for 10 minutes and washed three times with dH$_2$O and once with high salt buffer. A heterozygote control (known heterozygote, one to "normalize" or scale the RFUs and the other to confirm the correcting trending pattern observed in previously genotyped heterozygotes) and a negative control (no DNA) were included for each polymorphism. For background subtraction, L-histidine was used.

Tables 3-5 summarize the total number of participants for different age groups and the CYP2D6 inferred metabolic phenotype detected using the above procedure. Table 6 provides the particular 2D6 haplotypes that were observed in the patients that had antidepressant medication resistant subtypes of depression.

TABLE 3

Total Number of Participants in Each Grouping (All Ages; N = 86)
CYP2D6 Inferred Metabolic Phenotype

| | | Poor | Intermediate | Extensive | Ultra-Rapid |
|---|---|---|---|---|---|
| Response to Psychotropic | Non-Response | 5 | 16 | 6 | 0 |
| | Side-Effect | 5 | 16 | 7 | 0 |
| | Both | 8 | 17 | 5 | 1 |
| | Total | 18 | 49 | 18 | 1 |

TABLE 4

Total Number of Participants in Each Grouping (Ages: <19; N = 12)
CYP2D6 Inferred Metabolic Phenotype

| | | Poor | Intermediate | Extensive | Ultra-Rapid |
|---|---|---|---|---|---|
| Response to Psychotropic | Non-Response | 0 | 3 | 0 | 0 |
| | Side-Effect | 3 | 3 | 0 | 0 |
| | Both | 1 | 1 | 0 | 1 |
| | Total | 4 | 7 | 0 | 1 |

TABLE 5

Total Number of Participants in Each Grouping (Ages: >18; N = 74)
CYP2D6 Inferred Metabolic Phenotype

| | | Poor | Intermediate | Extensive | Ultra-Rapid |
|---|---|---|---|---|---|
| Response to Psychotropic Medication | Non-Response | 5 | 13 | 6 | 0 |
| | Side-Effect | 2 | 13 | 7 | 0 |
| | Both | 7 | 16 | 5 | 0 |
| | Total | 14 | 42 | 18 | 0 |

TABLE 6

Antidepressant Medication Resistant Subtypes of Depression[1]

| Sub# | 2D6 Haplo | 2D6 Enz Act |
|---|---|---|
| 100MR | *1/*2P Hz*2 | I |
| 101MR | Hz *4 | I |
| 102MR | *1/*10 H2*10 | I |
| 103MR | Hz *4 | I |
| 104MR | *2/*2P Homo *2 | I-P |
| 105MR | Hz *11 | I |
| 106MR | Hz *4 | I |
| 107MR | Homo *3 | None |
| 108MR | Hz *4 | I |
| 109MR | *2/*2 Homo *2 | I-P |
| 110MR | Hz *2 | I |
| 111MR | Hz *2 | I |
| 112MR | WT | N |
| 113MR | Hz *2 | I |

TABLE 6-continued

Antidepressant Medication Resistant Subtypes of Depression[1]

| Sub# | 2D6 Haplo | 2D6 Enz Act |
|---|---|---|
| 114MR | WT | N |
| 115MR | WT | N |
| 116MR | *3/*4 Compd Hz *3/*4 | P |
| 117MR | Hz *4 | I |
| 118MR | Hz *2 | I |
| 119MR | Compound Hz *2/*4 | P |
| 120MR | Hz *4 | I |
| 121MR | Hz *4 | I |
| 122MR | Hz *4 | I |
| 123MR | WT | N |
| 124MR | Hz *12 | I |
| 125MR | Hz *4 | I |
| 126MR | Hz *4 | I |
| 128MR | WT | N |
| 129MR | Hz *4 | I |
| 130MR | Hz *1E | N |
| 131MR | Homo *4 | P |
| 132MR | Hz *4 | I |
| 133MR | Hz *2 | I |
| 134MR | Compound Hz *2/*3 | P |
| 135MR | Compound Hz *3/*4 | P |
| 136MR | Hz * | I |
| 137MR | Hz *2 | I |
| 138MR | Compound Hz *2/*4 | P |
| 139MR | Compound Hz *2/*5 | P |
| 141MR | Homo *5 | None |
| 142MR | Compound Hz *4/*15 | P |
| 143MR | Hz *4 | I |
| 144MR | Hz *17 or *34 | I |
| 145MR | Hz *3 | I |
| 146MR | Compound Hz *4/*5 | P |
| 147MR | WT | N |
| 148MR | Hz *2 | I |
| 149MR | WT | N |
| 150MR | Hz *2 | I |
| 155MR | WT | N |
| 156MR | Hz *4 | I |
| 157MR | Hz *2 | I |
| 158MR | Hz *4 | I |
| 159MR | Hz *2 | I |
| 160MR | WT | N |
| 161MR | Hz *2 | I |
| 162MR | WT | N |
| 164MR | Hz *2 | I |
| 165MR | Hz *2 | I |
| 166MR | WT | N |
| 167MR | Compound Hz *2/*4 | P |
| 168MR | Compound Hz *2/*4 | P |
| 169MR | WT | N |
| 170MR | Hz *2 | I |
| 171MR | Compound Hz *2/*3 | P |
| 172MR | Hz *2 w/ duplication | Inc. act. |
| 173MR | Hz *2 | I |
| 174MR | Hz *4 w/ balanced duplication | N |
| 175MR | Hz *2 | I |
| 176MR | Hz *4 | I |
| 177MR | Hz *2 | I |
| 179MR | Homo *2 | I-P |
| 180MR | Homo *2 | I-P |
| 181MR | WT | N |
| 182MR | Hz *4 | I |
| 183MR | WT | N |
| 184MR | Hz *2 | I |
| 185MR | WT | N |
| 187MR | Compound Hz *2/*4 | P |
| 188MR | Hz *4 | I |
| 189MR | Hz *10 | I |
| 190MR | WT | N |
| 191MR | Hz *2 | I |
| 192MR | Hz *4 | I |
| 193MR | Hz *2 | I |
| 194MR | Hz *3 | I |
| 195MR | Hz *17 or *34 | I |
| 196MR | Hz *4 | I |
| 197MR | Compound Hz *2/*4 | P |
| 198MR | Hz *2 | I |
| 199MR | Compound Hz *2/*4 | P |

[1]P = poor, N = normal; I = intermediate; HI = Higher inducibility; WT = wild type All of these adolescents were found to have atypical 2D6 haplotypes (see Tables 3-5). The initial results of our analysis of the cytochrome P450 gene alleles in an adult sample also demonstrated a high degree of variability in the polymorphisms of the 2D6 gene (see Tables 3-5). Adolescents with polymorphisms associated with poor 2D6 metabolism were noted to have clinical histories marked by either a poor response to the medication or by a high frequency of side effects when they had been treated with the selective serotonin reuptake inhibitors that are metabolized by the 2D6 enzyme.

Example 2

Determining Genotype of the Dopamine Transporter, Dopamine Receptors, Tryptophan Hydroxylase, Serotonin Receptors, and COMT genes The following probes and primers of Table 7 can be generated to detect the genotype of the dopamine transporter (DAT1, SLC6A3), dopamine receptors (DRD1, DRD2, DRD3, DRD4, and DRD5), tryptophan hydroxylase (TPH), serotonin transporter (5-HTT), serotonin receptors (HTR1A, HTR1B, HTR1D, HTR2A, and HTR2C), and COMT genes.

| Symbol | Polymorphism | Forward Primer | Reverse Primer | Wt. Probe | Variant Probe | Stabilizer | SEQ ID |
|---|---|---|---|---|---|---|---|
| DAT1, SLC6A3 | >G710A, Q237R | CCCCCGCTGA CTCCCCTCTG | GACCCCCGAG CCTCACCTTC C | AGCTGCCACC | AGCTGCCACT | GCGGAGGCCC CAGGT | 29-33 |
|  | >C124T, L42F | ACCAAGAGGG AAGAAGCACA G | CCAATGACGG ACAGGAGAAA | GAGCTGGTGA G | GAGCTGGTGA A | CTGCACTCC GTTCTGCTC CT | 34-38 |
|  | 40 bp VNTR | GATGGGGGTC CTGGCTATGTC T | CTGGAGGTCA CGGCTCAAG |  |  |  | 39-40 |
| DRD1 | >T595G, S199A | GTGTGGCATG GACCTTGTCT G | GCAATGCGCC GTATTTGTTT C | AAAGCTTATT ACAGA | AGCTTATTAC AGC | GGATGAGAT GGCATATGT CCTGC | 41-45 |

-continued

| Symbol | Polymorphism | Forward Primer | Reverse Primer | Wt. Probe | Variant Probe | Stabilizer | SEQ ID |
|---|---|---|---|---|---|---|---|
| | >G150T, R50S | CCTGTTTCCT GTCGCTGCTC | CCAATACCTG TCCACGCTGAT | GGTGTCGGAA C | GGTGTCGGAA A | CTGATAACGC AGCACAGACC | 46-50 |
| | >C110G, T37R | GGGCTGGTGG TGGAGAG | TCTGACACAG CCAAGGAGATG | CCAGGAGCG | CCCAGGAGCC | TGGACAGGAT GAGCAGCGA A | 51-55 |
| | >A109C, T37P | GGGCTGGTGG TGGAGAG | TCTGACACAG CCAAGGAGATG | CCAGGAGCG T | CCAGGAGCGG | GGACAGGAT GAGCAGCGA CA | 56-60 |
| DRD2 | >A1051G, T351A | TCTCCACAGC ACTCCCGACA G | CCGAGAACAA TGGCGAGCAT C | GGTCCGGGT | GGTCCGGGC | TTTGCCATT GGGCATGGT CTG | 61-65 |
| | >C932G, S311C | CACCAGCCCA CCCGAGAG | ACCGAGAACA ATGGCGAGCA T | CCATGGTGG G | CCATGGTGG C | ACGGGTCGG GGAGAGTC | 66-70 |
| | >C928T, P310S | CCGGTACAGC CCCATCCC | GCCGACTCAC CGAGAACAAT G | GTGGGACGG | GGTGGGACG A | GTCGGGGAG AGTCAGCTG G | 71-75 |
| | >G460A, V154I | GGGGACAGGA GGGAGGGTTG AG | GAAGAGGAGT GGGCAGGAGA TGGTG | GGAGATCAT GAC | TGGAGATCA TGAT | GGTGACCCG GCGCTTG | 76-80 |
| DRD3 | >A25G, S9G | AGCAACCAAG CCCCAAAGAG | GAGCGCGCAG TAGGAGAGG | TTCAGGTGGC T | TCAGGTGGCC | ACTCAGCTGG CTCAGAGATG C | 81-85 |
| DRD4 | >T581G, V194G | CGCTACAACC GGCAGGGTGG G | GCAGCATGAG CGGGCAGGGT A | GGACGAGTA GA | GGACGAGTAG G | CCACGTAGTC GCGGTCCTC | 86-90 |
| | >C841G, P281A | CGCCTTCCCC CACGCCACC | GTTGGAGCCG CAGGGGTCCG | GGCGCGGG | GGCGCGGC | GGGCGCACAG TCGGG | 91-95 |
| DRD5 | >A889C, T297P | TGCGGTTTTC CATCAAGAAG | GGAGTTGGCC CAGCAGAA | CCGACAGGGT | CGACAGGGG | CTTGAGAACC TTGGTCTCCT TCTTGAT | 96-100 |
| | >G1252A, V418I | CAACGCCGAC TTCTGGAA | ACATGCGATC GAAAGGACTC T | CGGGGGGAAC | CGGGGGGAAT | GGCGTTGGGC ATCATGTGG | 101-105 |
| | >G181A, V61M | GCAGTCCAGC CCGAAATG | GCACGATGGC TGCGGA | CTGCGGACAC | CTGCGGACAT | CAGCACGTTG CCCAG | 106-110 |
| | >G185C, C62S | CAACGTGCTG GTG | CATCTTGCGC TTGTA | GGCTGCGC | TGGCTGCG | ACACCAGCAC GTTGTA | 111-115 |
| | >T263G, R88L | CGCCAAGATG ACCAAC | CGGAATGAAG GAGATGA | GCCACGAAGA | GCCACGAAGC | GGTCTGACAC AGCAGAGAC A | 116-120 |
| | >G1354A, W455- | GCAGCTGCCT ACATCCACAT | CATTCGGGGT GAAAGGTGTT A | GTCCAGCTCC | GTCCAGCTCT | CAGACAGACT CTGCAACAGG GTC | 121-125 |
| HTR1A | >G815A, G272D | GGAGAGTCGG GGAGCAGGAA C | GAGGCGGGGG CACAAGG | GCACAGAGCA C | GCACAGAGCA T | CCCCAGCCTT GCTCTCCA | 126-130 |
| | >G656T, R219L | CTACATCCCG CTGCTGCTCA T | CCTGCTCCCC GACTCTCCA | GCGCAGCTC | GCGCAGCTA | GGAATATGCG CCCATAGAGA ACCA | 131-135 |
| | >C548T, P551L | GCTCACTTGG CTTATTGGCT TCCTC | CATGAGCAGC AGCGGGATGT | CATGCGTCGG | CATGCGTCGA | GGTCCGAGCG GTCTTCCG | 136-140 |
| | >A82G, I28V | AGGGCAACAA CACCACATCA CCAC | GCAGCACCAA CACCGACACC AT | ACGTCGGAGA T | CGTCGGAGAC | ACCAGTAGTG TTGCCGCCG | 141-145 |
| | >G64A, G22S | TCAGGGCAAC AACACCACAT | GCACCAACAC CGACACCA | GTTGCCGCC | GTTGCCGCT | GGTCTCAAAG GGAGCCGGT | 146-150 |
| | >C47T, P16L | TTTTCTTCCC TCCCCCTTCC | CCACCACGCA CGCATTG | AAGGGAGCCG | AAAGGGAGCC A | GTGGTGATGT GGTGTTGTTG CC | 151-155 |
| HTR2A | T102C | GCTCAACTAC GAACTCCCTA A | TCACTACGGC TGTCAGTAAA G | TTAGCTTCTC CA | TTAGCTTCTC CG | GAGTTAAAGT CATTACTGTA GAGCCTGGT | 156-160 |
| HTR1D | >C794T, S265L | GCTCTGCTCG CTCAAC | GATTTAGTG GCTTTCCTTT C | CCGAGTGCG | GCCGAGTGCA | AGTGCCCCTC ATGGAGGC | 161-165 |

-continued

| Symbol | Polymorphism | Forward Primer | Reverse Primer | Wt. Probe | Variant Probe | Stabilizer | SEQ ID |
|---|---|---|---|---|---|---|---|
| HTR2C | >C10G, L4V | CTCAATTTTA AACTTTGGTT GCTTA | TTTTGAATAG GAAACACCCA TAA | GCATTCCTCA G | GCATTCCTCA C | GTTCACCATG ATTGCTTCAG TCTTAAGC | 166-170 |
|  | >G68C, C23S | ATGATGACAA TGATGCTGAT GATGATAATG | TCCACCATCG GAGGTATTGA AAATG | TCACAGAAAT ATCAC | CACAGAAATA TCAG | ATTGCCAAAC CAATAGGCCA ATTAGG | 171-175 |
| CYP1A2*IF | -164C > A | GGCTTCAGTT TCCCGATCTG | TAGGCAAGGG CAGGCACTAC | AAGGAGCTGG | GAAGGAGCTG A | GTACATGGGG GCCCCC | 176-180 |

Example 3

The genotype of the CYP2D6, CYP2C19, and 5HTTR genes was determined in 97 patients using the methods described above. As indicated in Example 1, CYP2D6 *2, *3, *4, *10, *17, and *5 del alleles, CYP2C19 *2 (A,B), *3, *4, *5 (A,B), *6, *7, and *8 alleles, and the short/long form of the 5HTTR gene were assessed.

Each patient that was genotyped exhibited either a poor response to at least one antidepressant medication or an intolerable side effect to at least one antidepressant medication. Based on the genotype information, 18 medication profiles were generated (Table 8). In Table 8, PM is poor metabolizer; IM is intermediate metabolizer; EM is extensive metabolizer; s is the short form of the gene; and l is the long form of the gene. Each medication profile provides antidepressant medications that are acceptable for use, antidepressant medications to be used with caution, and antidepressant medications to be avoided or used with caution and close monitoring.

TABLE 8

Medication Algorithm Microarray Results from Pharmacological Study

| Key Gene Genotype Category | 2D6 | 2C19 | 5HTTR | Genotype frequencies in pharmacological study |
|---|---|---|---|---|
| Med Profile 1 | PM | PM | s/s | 2 |
| Med Profile 2 | PM | PM | s/l | 2 |
| Med Profile 3 | PM | PM | l/l | 1 |
| Med Profile 4 | PM | EM | s/s | 1 |
| Med Profile 5 | PM | EM | s/l | 6 |
| Med Profile 6 | PM | EM | l/l | 1 |
| Med Profile 7 | IM | PM | s/s | 1 |
| Med Profile 8 | IM | PM | s/l | 7 |
| Med Profile 9 | IM | PM | l/l | 3 |
| Med Profile 10 | EM | PM | s/s | 0 |
| Med Profile 11 | EM | PM | s/l | 6 |
| Med Profile 12 | EM | PM | l/l | 3 |
| Med Profile 13 | IM | EM | s/s | 2 |
| Med Profile 14 | IM | EM | s/l | 17 |
| Med Profile 15 | IM | EM | l/l | 16 |
| Med Profile 16 | EM | EM | s/s | 7 |
| Med Profile 17 | EM | EM | s/l | 10 |
| Med Profile 18 | EM | EM | l/l | 12 |

Medication profile 1 is associated with 2D6 and 2C19 poor metabolizers and the s/s form of the 5HTTR gene. In patients with medication profile 1, bupropion is acceptable for use, mirtazapine and fluvoxamine can be used with caution, while citalopram, escitalopram, paroxetine, fluoxetine, venlafaxine, amitriptyline, imipramine, nortriptyline, and sertraline should be avoided or used with caution and close monitoring.

Medication profile 2 is associated with 2D6 and 2C19 poor metabolizers and the s/l form of the 5HTTR gene. In patients with medication profile 2, fluvoxamine and bupropion are acceptable for use, sertraline and mirtazapine can be used with caution, and citalopram, escitalopram, paroxetine, fluoxetine, venlafaxine, amitriptyline, imipramine, and nortriptyline should be avoided or used with caution and close monitoring.

Medication profile 3 is associated with 2D6 and 2C19 poor metabolizers and the l/l form of the 5HTTR gene. In patients with medication profile 3, fluvoxamine and bupropion are acceptable for use, sertraline and mirtazapine can be used with caution, and citalopram, escitalopram, paroxetine, fluoxetine, venlafaxine, amitriptyline, imipramine, and nortriptyline should be avoided or used with caution and close monitoring.

Medication profile 4 is associated with 2D6 poor metabolizers, 2C19 extensive metabolizers, and the s/s form of the 5HTTR gene. In patients with medication profile 4, bupropion is acceptable for use, mirtazapine, citalopram, fluvoxamine, and escitalopram can be used with caution, and paroxetine, fluoxetine, venlafaxine, amitriptyline, imipramine, nortriptyline, and sertraline should be avoided or used with caution and close monitoring.

Medication profile 5 is associated with 2D6 poor metabolizers, 2C19 extensive metabolizers, and the s/s form of the 5HTTR gene. In patients with medication profile 5, citalopram, fluvoxamine, bupropion and escitalopram are acceptable for use, sertraline and mirtazapine can be used with caution, and paroxetine, fluoxetine, venlafaxine, amitriptyline, imipramine, and nortriptyline should be avoided or used with caution and close monitoring.

Medication profile 6 is associated with 2D6 poor metabolizers, 2C19 extensive metabolizers, and the l/l form of the 5HTTR gene. In patients with medication profile 6, citalopram, fluvoxamine, bupropion and escitalopram are acceptable for use, sertraline and mirtazapine can be used with caution, and paroxetine, fluoxetine, venlafaxine, amitriptyline, imipramine, and nortriptyline should be avoided or used with caution and close monitoring.

Medication profile 7 is associated with 2D6 intermediate metabolizers, 2C19 poor metabolizers, and the s/s form of the 5HTTR gene. In patients with medication profile 7, bupropion is acceptable for use, mirtazapine, venlafaxine, amitriptyline, nortriptyline, fluvoxamine, and sertraline can be used with caution, and citalopram, escitalopram, fluoxetine, imipramine, and paroxetine should be avoided or used with caution and close monitoring.

Medication profile 8 is associated with 2D6 intermediate metabolizers, 2C19 poor metabolizers, and the s/l form of the 5HTTR gene. In patients with medication profile 8, fluvoxamine, bupropion, and sertraline are acceptable for use, mirtazapine, paroxetine, venlafaxine, amitriptyline, and nortriptyline can be used with caution, and citalopram, escitalopram, fluoxetine, and imipramine should be avoided or used with caution and close monitoring.

Medication profile 9 is associated with 2D6 intermediate metabolizers, 2C19 poor metabolizers, and the l/l form of the 5HTTR gene. In patients with medication profile 9, fluvoxamine, bupropion, and sertraline are acceptable for use, mirtazapine, paroxetine, venlafaxine, amitriptyline, and nortriptyline can be used with caution, and citalopram, escitalopram, fluoxetine, and imipramine should be avoided or used with caution and close monitoring.

Medication profile 10 is associated with 2D6 extensive metabolizers, 2C19 poor metabolizers, and the s/s form of the 5HTTR gene. In patients with medication profile 10, bupropion and venlafaxine are acceptable for use, mirtazapine, nortriptyline, imipramine, amitriptyline, sertraline, paroxetine, and fluoxetine can be used with caution, and fluvoxamine, citalopram, and escitalopram should be avoided or used with caution and close monitoring.

Medication profile 11 is associated with 2D6 extensive metabolizers, 2C19 poor metabolizers, and the s/l form of the 5HTTR gene. In patients with medication profile 11, sertraline, venlafaxine, paroxetine, bupropion, and fluoxetine are acceptable for use, and mirtazapine, fluvoxamine, nortriptyline, citalopram, escitalopram, imipramine, and amitriptyline can be used with caution.

Medication profile 12 is associated with 2D6 extensive metabolizers, 2C19 poor metabolizers, and the l/l form of the 5HTTR gene. In patients with medication profile 12, sertraline, venlafaxine, paroxetine, bupropion, and fluoxetine are acceptable for use, and mirtazapine, fluvoxamine, nortriptyline, citalopram, escitalopram, imipramine, and amitriptyline can be used with caution.

Medication profile 13 is associated with 2D6 intermediate metabolizers, 2C19 extensive metabolizers, and the s/s form of the 5HTTR gene. In patients with medication profile 13, bupropion and mirtazapine are acceptable for use, venlafaxine, amitriptyline, imipramine, nortriptyline, citalopram, fluvoxamine, escitalopram, and sertraline can be used with caution, and paroxetine and fluoxetine should be avoided or used with caution and close monitoring.

Medication profile 14 is associated with 2D6 intermediate metabolizers, 2C19 extensive metabolizers, and the s/l form of the 5HTTR gene. In patients with medication profile 14, citalopram, fluvoxamine, bupropion, escitalopram, sertraline, and mirtazapine are acceptable for use, and paroxetine, fluoxetine, venlafaxine, amitriptyline, imipramine, and nortriptyline can be used with caution.

Medication profile 15 is associated with 2D6 intermediate metabolizers, 2C19 extensive metabolizers, and the l/l form of the 5HTTR gene. In patients with medication profile 15, citalopram, fluvoxamine, bupropion, escitalopram, sertraline, and mirtazapine are acceptable for use, and paroxetine, fluoxetine, venlafaxine, amitriptyline, imipramine, and nortriptyline can be used with caution.

Medication profile 16 is associated with 2D6 extensive metabolizers, 2C19 extensive metabolizers, and the s/s form of the 5HTTR gene. In patients with medication profile 16, bupropion, mirtazapine, venlafaxine, amitriptyline, imipramine, and nortriptyline are acceptable for use, and paroxetine, fluoxetine, fluvoxamine, sertraline, escitalopram, and citalopram can be used with caution.

Medication profile 17 is associated with 2D6 extensive metabolizers, 2C19 extensive metabolizers, and the s/l form of the 5HTTR gene. Medication profile 18 is associated with 2D6 extensive metabolizers, 2C19 extensive metabolizers, and the l/l form of the 5HTTR gene. In patients with medication profiles 17 or 18, citalopram, fluvoxamine, bupropion, escitalopram, sertraline, mirtazapine, paroxetine, fluoxetine, venlafaxine, amitriptyline, imipramine, and nortriptyline are acceptable for use.

Example 4

The genotype of the CYP2D6, CYP2C19, CYP3A4, CYP1A2, and HTR2A genes was determined in ten patients using the methods described above. The genotype of the 5HTTR gene was determined by amplifying the polymorphic region of the gene using primers flanking the region. Reaction products were sized using electrophoresis (Agilent Technologies). CYP3A4*1B, *2, *5, *6, *12, *13, *15A, *17, and *18A alleles, CYP1A2*1F allele, and the HTR2A 102 polymorphism were detected Based on the CYP2D6 genotype, patients were classified as being poor, intermediate, extensive, or ultra rapid metabolizers. For each of the CYP2C19, CYP3A4, and CYP1A2 genotypes, patients were classified as being either extensive or not extensive (i.e., poor) metabolizers. For the 5HTTR genotype, patients were classified as having the short/short (s/s) form of the gene, the short/long (s/l) form of the gene, or the long/long (l/l) form of the gene. For the HR2A genotype, patients were classified as having either the C/C allele or as having the T/T or T/C alleles.

The following six rules were used to sort the genotypes into 192 treatment recommendations. The first rule relates to the CYP2D6 genotype. For poor metabolizers and ultra rapid metabolizers, CYP2D6 substrates were placed in the "use very cautiously with close monitoring" category. For intermediate metabolizers, exclusive CYP2D6 substrates were placed in the "avoid or use very cautiously with close monitoring" category. For intermediate metabolizers, substrates that are partially metabolized by CYP2D6 were placed in the "use cautiously" category. For extensive metabolizers, CYP2D6 substrates were placed in the "acceptable for use" category.

After applying the first rule, the second rule relating to the 2C19 genotype was applied. For poor metabolizers based on their CYP2C19 genotype, exclusive CYP2C19 substrates were placed in the "avoid or use very cautiously with close monitoring" category. For extensive or intermediate metabolizers based on their CYP2C19 genotype, CYP2C19 substrates were placed in the "acceptable for use" category. Substrates that are primarily metabolized by both CYP2D6 and CYP2C19 were placed in the "avoid or use very cautiously with close monitoring" category if CYP2C19 was poor and CYP2D6 was either intermediate or poor, or placed in the "use cautiously" category if CYP2C19 was poor and CYP2D6 was extensive.

A third rule relating to the 3A4 genotype was applied after the first and second rules were applied. For poor metabolizers based on their CYP3A4 genotype, exclusive CYP3A4 substrates were placed in the "avoid or use very cautiously with close monitoring" category. For extensive or intermediate metabolizers based on their CYP3A4 genotype, CYP3A4 substrates were placed in the "acceptable for use" category. Substrates that are primarily metabolized by any two of the following three enzymes: CYP2D6, CYP2C19, or CYP3A4, were placed in the "avoid or use very cautiously with close monitoring" category if any two of the three were intermediate or poor metabolizers or placed in the "use cautiously" category if one of the two most primary enzymes was a poor metabolizer.

The fourth rule relating to the 1A2 genotype was applied after applying the first three rules. For poor metabolizers based on CYP1A2 genotype, CYP1A2 substrates were placed in the "avoid or use very cautiously with close monitoring" category (include fluvoxamine as a primary CYP1A2 substrate). For poor metabolizers based on the CYP1A2 genotype, substrates having the CYP1A2 pathway as one of their primary pathways were placed in the "use with caution" category.

After applying the first four rules, the fifth rule relating to the 5HTTR genotype was applied. For the homozygous short genotype (s/s) of the serotonin transporter gene, SSRI's that were categorized as "acceptable for use" were shifted to the "use with caution" category. For the homozygous short genotype (s/s) of the serotonin transporter gene, SSRI's that were categorized as "use with caution" were shifted to the "avoid or use very cautiously with close monitoring" category. Antidepressants, outside the SSRI class, do not shift category based on 5HTTR genotype.

Rule six, which relates to the HR2A genotype, was applied after applying the first five rules. For the "mutant form" of the 5-hydroxytryptamine serotonin receptor 2A gene, if paroxetine was in the "acceptable for use" category, it was shifted to the "use with caution" category. If paroxetine was in the "use with caution" category, it was shifted to the "avoid or use very cautiously with close monitoring.

Based on the genotype of the patients and associated medication profile, medications appropriate for the patient were selected. Table 9 summarizes the data for the 10 patients. Case studies of four of the seven patients are presented below.

The first case is a 16-year-old white female who was genotyped and found to be a poor metabolizer for CYP2D6 (*3/*9) as well as being a poor metabolizer for CYP2C19 (*2/*2). She was diagnosed at 6 years of age as having ADHD and treated unsuccessfully. She subsequently developed symptoms of depression and mood dysregulation and was placed on many medications that were metabolized by CYP2D6, such as EFFEXOR. Additionally, she was homozygous for a short form of the serotonin transporter gene. Based on her specific genotype of these key genes, the algorithm demonstrates that there are a relatively small number of potential strategies for controlling her depression. The medication profile generated based on her genotype of R2A TT/TC, s/s form of 5HTTR, extensive metabolizer for 1A2 and 3A4, and poor metabolizer for 2C19 and 2D6 indicated that bupropion was acceptable for use, mirtazapine and fluoxamine should be used with caution, and citalopram, escitalopram, paroxetine, fluoxetine, venlafaxine, amitriptyline, imipramine, nortriptyline, and sertraline should be avoided or used with caution and monitoring.

Before genotyping, she had a particularly unusual side effect to citalopram in that she developed hallucinations (incidence less than 1%). This atypical and dangerous side effect could have been avoided if she had been genotyped prior to receiving this medication. The metabolic enzyme that is primarily involved in the metabolism of citalopram is CYP2C19 and a secondary metabolic pathway is CYP2D6. Both of these pathways were nonfunctional in this patient. Therefore, even on a modest dose of citalopram, this patient developed acute auditory and visual hallucinations, which were subsequently treated with an atypical antipsychotic medication. Additionally, based on an inability to develop an effective treatment plan for this patient, she required three acute hospitalizations and a partial hospitalization experience prior to being referred to a state hospital for two months. She was unsuccessfully tried on more than a dozen psychotropic medications. There is no question that her care could have been greatly improved and perhaps some of her hospitalizations could have been avoided if clinicians had been aware of her inability to use many of the drugs that had been prescribed at their standard doses. Additionally, her serotonin transporter genotype (C/C) would have suggested a poor response to many of the medications that had been prescribed. Subsequent to genotyping, she was placed on a combination of two mood stabilizers that are metabolized by an alternative pathway (LAMICTAL (lamotrigine) and TRILEPTAL (oxcarbazepine)). She is also tolerating treatment with ABILIFY (aripiprazole), which in addition to being metabolized by CYP2D6 is metabolized by CYP3A4, for which she has an internal metabolic pathway. She is now doing reasonably well.

The second case is a 42-year-old Caucasian female with a persistent depressive illness and pervasive anxiety and a long-standing history of psychotropic medication intolerance. This patient had a comprehensive neurological evaluation, which failed to provide an organic explanation for her symptoms. This patient has been treated with at least nine psychotropic medications in the past. Striking examples of CYP2D6 intolerance include the development of acute hallucinations while taking paroxetine and a very low tolerance to amitriptyline. This patient had poor CYP2D6 metabolism and intermediate CYP2C19 metabolism. This represents a rare genotype that would suggest difficulties in tolerating treatment with citalopram. Indeed, she did have irritability and lethargy when taking citalopram. To compound this problem, she also was homozygous for the short form of the serotonin transporter, which is associated with a poor response to serotonin receptive inhibitors. She had experienced multiple outpatient visits for her psychiatric problems. Awareness of her genotype earlier in her history would clearly have allowed her clinician to avoid a number of medications that she could not tolerate. The medication profile generated based on her genotype of HR2A TT/TC, s/s form of 5HTTR, extensive metabolizer for 1A2 and 3A4, and poor metabolizer for 2C19 and 2D6 indicated that bupropion was acceptable for use, mirtazapine and fluoxamine should be used with caution, and citalopram, escitalopram, paroxetine, fluoxetine, veulafaxine, amitriptyline, imipramine, nortriptyline, and sertraline should be avoided or used with caution and monitoring.

The third case history is a 67-year-old woman with a diagnosis of major depressive disorder, who had been treated with seven different medications in the past. These had not been effective, and she had required two psychiatric hospitalizations. It was determined that she was a poor metabolizer for both CYP2D6 (*4/*9) and CYP2C19 (*2/*2). Additionally, she was homozygous for the long form of the serotonin transporter gene. Based on her genotype of HR2A C/C, l/l form of 5HTTR, extensive metabolizer for 1A2 and 3A4, and poor metabolizer for 2C19 and 2D6, the associated medication profile indicated that fluoxamine and bupropion were acceptable for use, sertraline and mirtazapine should be used with caution, and citalopram, escitalopram, paroxetine, fluoxetine, venlafaxine, amitriptyline, imipramine, and nortriptyline should be avoided or used with caution and monitoring. If her genotype had been known, it would have been possible to anticipate that she would have had side effects to both EFFEXOR (Venlafaxine) and LEXAPRO (escitalopram oxalate). This could have been predicted, given that two of the three metabolic pathways involved in the metabolism of LEXAPRO were completely inactive. Subsequent to her genotyping, she was successfully treated with electroconvulsive therapy (ECT) and concurrently successfully treated with REMERON (mirtazapine), trazodone, and KLONOPIN (clonazepam), which have alternative pathways of metabolism to CYP2D6 and CYP2C19.

The fourth case is a 50-year-old Caucasian woman who had been diagnosed as having dysthymia and chronic anxiety. She had been placed on multiple psychotropic drugs, including two CYP2D6 medications that she could not tolerate. Her genotype indicated that she was a poor CYP2D6 metabolizer (*4/*4) and an intermediate CYP2C19 metabolizer (*1/*2). She was heterozygous for the long and short form of the serotonin transporter gene. Based on her genotype of HR2A C/C, l/s form of 5HTTR, extensive metabolizer for 1A2 and 3A4, and poor metabolizer for 2C19 and 2D6, the associated medication profile indicated that fluoxamine and bupropion were acceptable for use, sertraline and mirtazapine should be used with caution, and citalopram, escitalopram, paroxetine, fluoxetine, venlafaxine, amitriptyline, imipramine, and nortriptyline should be avoided or used with caution and monitoring.

This patient had multiple hospitalizations at considerable cost. She also found it difficult to tolerate a range of nonpsychiatric medications, including being able to take only one dose of PROZAC (fluoxetine) and ZOLOFT (sertraline) before finding that she was acutely uncomfortable. Of particular interest, she ultimately responded to a subclinical dose of paroxetine, which represents an example of using the algorithm to find a method to administer an effective medication that in normal doses could not have been tolerated.

Based on patient no. 5's genotype of HR2A C/C, l/l form of 5HTTR, extensive metabolizer for 1A2 and 3A4, and poor metabolizer for 2C19 and 2D6, the associated medication profile indicated that fluoxamine and bupropion were acceptable for use, sertraline and mirtazapine should be used with caution, and citalopram, escitalopram, paroxetine, fluoxetine, venlafaxine, amitriptyline, imipramine, and nortriptyline should be avoided or used with caution and monitoring.

The medication profile associated with patient no. 6's genotype (HTR2A CC; 5HTTR l/s; 1A2, 3A4, and 2D6 extensive; and 2C19 poor) indicates that sertraline, venlafaxine, bupropion, and fluoxetine are acceptable for use, and mirtazapine, fluvoxamine, nortriptyline, citalopram, escitalopram, imipramine, amitriptyline, and paroxetine can be used with caution.

The medication profile associated with patient no. 7's genotype (HTR2A TT/TC; 5HTTR l/s; 1A2, 3A4, and 2C19 extensive; and 2D6 ultra rapid) indicates that citalopram, fluvoxamine, bupropion, and escitalopram are acceptable for use; sertraline and mirtazapine can be used with caution, and paroxetine, fluoxetine, venlafaxine, amitriptyline, imipramine, and nortriptyline should be avoided or used with caution and close monitoring.

The medication profile associated with patient no. 8's genotype (HTR2A TT/TC; 5HTTR l/l; 1A2, 3A4, and 2C19

TABLE 9

| Sub. No | Age | Gender | Race | Diagnosis | 2D6 | 2C19 | 3A4 | 1A2 | 5HTTR | HTR2A T102C |
|---|---|---|---|---|---|---|---|---|---|---|
| 1 | 16 | F | Cauc. | ADHD; adjustment disorder NOS; Depression NOS; Psychosis NOS; Bipolar Disorder | 3/9 Poor Freq: *3 = 1% *9 = 3% | 2/2 Poor Freq: *2 = 14% | *1*1 | *1/*1F | s/s | TC |
| 2 | 42 | F | Cauc. | Generalized anxiety disorder; Depressive Disorder NOS; Panic disorder | 4/4 Poor Freq: *4 = 18% | 1/2 Poor Freq: *1 = 86% *2 = 14% | *1*1 | *1/*1F | s/s | TC |
| 3 | 67 | F | Other | Major depressive disorder | 4/9 Poor Freq: *9 = 3% | 2/2 Poor Freq: *2 = 14% | *1*1 | *1/*1 | l/l | CC |
| 4 | 50 | F | Cauc. | Panic disorder; generalized anxiety disorder; dysthymia, somatogorm disorder NOS | 4/4 Poor Freq. *4 = 18% | 1/2 Int. Freq: *1 = 86% *2 = 14% | *1*1 | *1/*1F | s/l | CC |
| 5 | 39 | F | Cauc. | Generalized anxiety disorder | 3/4 Poor Freq. *3 = 33% *4 = 18% | 1/2 Poor Freq: *1 = 86% *2 = 14% | *1*1 | *1/*1F | l/l | CC |
| 6 | 12 | F | Hispanic | Bipolar disorder NOS | 1/1 ext. freq. *1 = 37% | 1/2 Int. Freq. *1 = 86% *2 = 14% | *1/*1B | *1/*1 | S/l | CC |
| 7 | 54 | M | | Bipolar disorder | 2P/2P ext. freq: *2P = unk. | 1/1 Ext. Freq: *1 = 86% | *1*1 | *1/*1F | s/l | TC |
| 8 | 47 | F | Cauc. | Major depressive psychotic | 1/5 Int. *1 = 37% *5 = 4% | 1/1 Ext. *1 = 37% | *1/*1B | *1/*1 | l/l | TC |
| 9 | 25 | F | Cauc. | Panic disorder | 2/2P ext. freq: *2 = 33% *2P = unk. | 1/1 Ext. Freq: *1 = 37% | *1*1 | *1/*1 | s/l | TC |
| 10 | 16 | F | Asian-American | Major depressive disorder vs. bipolar | 4/10 Poor Freq: *4 = 18% *10 = 2% | 1/1 Ext. Freq: *1 = 86% | *1*1 | *1F/*1P | s/l | TT | extensive; and 2D6 intermediate) indicates that citalopram, fluvoxamine, bupropion, escitalopram, sertraline, and mirtazapine are acceptable for use; and paroxetine, fluoxetine, venlafaxine, amitriptyline, imipramine, and nortriptyline should be avoided or used with caution and close monitoring.

The medication profile associated with patient no. 9's genotype (HTR2A TT/TC; 5HTTR l/s; and 1A2, 3A4, 2C19, and 2D6 extensive) indicates that citalopram, fluvoxamine, bupropion, escitalopram, sertraline, mirtazapine, paroxetine, fluoxetine, venlafaxine, amitriptyline, imipramine, and nortriptyline are acceptable for use.

The medication profile associated with patient no. 10's genotype (HTR2A TT/TC; 5HTTR l/s; 1A2, 3A4, and 2C19 extensive; and 2D6 poor) indicates that citalopram, fluvoxamine, bupropion, and escitalopram are acceptable for use, sertraline and mirtazapine should be used with caution, and paroxetine, fluoxetine, venlafaxine, amitriptyline, imipramine, and nortriptyline should be avoided or used with caution and close monitoring.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims

---

What is claimed is:

1. A method of administering an antidepressant medication to a patient in need thereof comprising:
   (1) determining the patients genotype for a panel of genes comprising the following:
      (a) a cytochrome P450 CYP2D6 gene consisting of two alleles independently selected from the group consisting of fully functional alleles 2D6*1A, *2, *2N, and *35, partially functional alleles 2D6*10 and *17, and non-functional alleles 2D6*3, *4, *5, *6, *7, *8, and *12,
      (b) a cytochrome P450 CYP2C19 gene consisting of two alleles independently selected from the group consisting of fully functional alleles 2C19*1A and *1B, and non-functional alleles 2C19*2A, *2B, *3, *4, *5A, *5B, *6, *7 and *8, and
      (c) a serotonin transporter gene 5HTTR consisting of two alleles independently selected from the short (s) and long (l) forms of the 5HTTR gene;
   (2) assigning a metabolic phenotype to the patient based on the genotype of the cytochrome P450 genes in (1), wherein the metabolic phenotype is selected from poor (P), intermediate (I), and extensive (E), and said phenotype is assigned based upon the number of functional alleles for each cytochrome P450 gene as follows: P=no fully functional alleles and either one or no partially functional alleles, I=either one fully functional allele and a non-functional allele or two partially functional alleles, and E=either one fully functional allele and one partially functional allele or two fully functional alleles; and
   (3) administering to the patient an antidepressant medication selected from the group consisting of:
      (i) bupropion, mirtazapine, fluvoxamine and sertraline if the patient's metabolic phenotype is P/P (poor for both 2D6 and 2C19) and the 5HTTR genotype is heterozygous (l/s) or homozygous (l/l);
      (ii) bupropion, mirtazapine and fluvoxamine if the patient's metabolic phenotype is P/P and the 5HTTR genotype is homozygous (s/s);
      (iii) bupropion, mirtazapine, fluvoxamine, sertraline, amitriptyline, nortriptyline, venlafaxine and paroxetine if the patient's metabolic phenotype is I/P (intermediate for 2D6 and poor for 2C19) and the 5HTTR genotype is heterozygous (l/s) or homozygous (l/l);
      (iv) bupropion, mirtazapine, fluvoxamine, sertraline, amitriptyline, nortriptyline and venlafaxine, if the patient's metabolic phenotype is I/P and the 5HTTR genotype is homozygous (s/s);
      (v) bupropion, mirtazapine, citalopram, escitalopram, fluvoxamine and sertraline if the patient's metabolic phenotype is P/E (poor for 2D6 and extensive for 2C19) and the 5HTTR genotype is heterozygous (l/s) or homozygous (l/l);
      (vi) bupropion, mirtazapine, citalopram, escitalopram, and fluvoxamine if the patient's metabolic phenotype is P/E and the 5HTTR genotype is homozygous (s/s);
      (vii) bupropion, venlafaxine, amitriptyline, imipramine, mirtazapine, nortriptyline, fluoxetine, paroxetine, sertraline, citalopram, escitalopram and fluvoxamine if the patient's metabolic phenotype is E/P (extensive for 2D6 and poor for 2C19), and the 5HTTR genotype is heterozygous (l/s) or homozygous (l/l);
      (viii) bupropion, venlafaxine, amitriptyline, imipramine, mirtazapine, nortriptyline, fluoxetine, paroxetine and sertraline if the patient's metabolic phenotype is E/P and the 5HTTR genotype is homozygous (s/s);
      (ix) bupropion, mirtazapine, escitalopram, sertraline, amitriptyline, imipramine, nortriptyline, venlafaxine, citalopram, fluvoxamine, fluoxetine and paroxetine, if the patient's metabolic phenotype is I/E (intermediate for 2D6 and extensive for 2C19) and the 5HTTR genotype is heterozygous (l/s) or homozygous (l/l);
      (x) bupropion, mirtazapine, escitalopram, sertraline, amitriptyline, imipramine, nortriptyline, venlafaxine, citalopram and fluvoxamine, if the patient's metabolic phenotype is I/E and the 5HTTR genotype is homozygous (s/s); and
      (xi) amitriptyline, bupropion, citalopram, fluvoxamine, imipramine, mirtazapine, nortriptyline, venlafaxine, escitalopram, fluoxetine, paroxetine and sertraline if the patient's metabolic phenotype is E/E (extensive for both 2D6 and 2C19) and the 5HTTR genotype is heterozygous (l/s) or homozygous (s/s or l/l).

2. A method of administering an antidepressant medication to a patient in need thereof comprising:
   (1) determining the patients genotype for following panel of genes:
      (a) a cytochrome P450 CYP3A4 gene consisting of two alleles independently selected from the group consisting of fully functional alleles 3A4*1A, *1B, *2, *5, *6, and *15A, partially functional alleles 3A4*12, *13 and *17, and increased functional alleles 3A4*18A,
      (b) a cytochrome P450 CYP1A2 gene consisting of two alleles independently selected from the group consisting of fully functional alleles 1A2*1A, partially functional alleles 1A2*3, and increased functional alleles 1A2*1F, and
(c) a cytochrome P450 CYP2D6 gene consisting of two alleles independently selected from the group consisting of fully functional alleles 2D6*1A, *2, *2N, and *35, partially functional alleles 2D6*10 and *17, and non-functional alleles 2D6*3, *4, *5, *6, *7, *8, and *12,
(d) a cytochrome P450 CYP2C19 gene consisting of two alleles independently selected from the group consisting of fully functional alleles 2C19*1A and *1B, and non-functional alleles 2C19*2A, *2B, *3, *4, *5A, *5B, *6, *7 and *8, and
(e) a serotonin transporter gene 5HTTR consisting of two alleles independently selected from the short (s) and long (l) forms of the 5HTTR gene;
(f) a serotonin receptor gene HTR2A T102C polymorphism consisting of two alleles independently selected from the normal (T) and mutant (C) forms of the HTR2A gene;
(2) assigning a metabolic phenotype to the patient based on the genotype of the cytochrome P450 genes in (1), wherein the metabolic phenotype is selected from poor (P), intermediate (I), and extensive (E), and said phenotype is assigned based upon the number of functional alleles for each cytochrome P450 gene as follows: P=either two partially functional alleles or two increased functional alleles, I=either one fully functional allele and a partially functional allele or one fully functional allele and an increased functional allele, and E=either one partially functional allele and one increased functional allele or two fully functional alleles; and
(3) administering to the patient an antidepressant medication selected from the group consisting of:
  (i) bupropion, mirtazapine, fluvoxamine and sertraline if the patient's metabolic phenotype is P/P (poor for both 2D6 and 2C19), P, I or E for 3A4, I or E for 1A2, the HTR2A genotype is heterozygous (T/C) or homozygous (T/T or C/C) and the 5HTTR genotype is heterozygous (l/s) or homozygous (l/l);
  (ii) bupropion, mirtazapine, and sertraline if the patient's metabolic phenotype is P/P for 2D6 and 2C19, P, I or E for 3A4, P for 1A2, the HTR2A genotype is heterozygous (T/C) or homozygous (T/T or C/C) and the 5HTTR genotype is heterozygous (l/s) or homozygous (l/l);
  (iii) bupropion, mirtazapine and fluvoxamine if the patient's metabolic phenotype is P/P for 2D6 and 2C19, P, I or E for 3A4, E for 1A2, the HTR2A genotype is heterozygous (T/C) or homozygous (T/T or C/C) and the 5HTTR genotype is homozygous (s/s);
  (iv) bupropion and mirtazapine if the patient's metabolic phenotype is P/P for 2D6 and 2C19, P, I or E for 3A4, I or P for 1A2, the HTR2A genotype is heterozygous (T/C) or homozygous (T/T or C/C) and the 5HTTR genotype is homozygous (s/s);
  (v) bupropion, mirtazapine, fluvoxamine, sertraline, amitriptyline, nortriptyline, venlafaxine and paroxetine if the patient's metabolic phenotype is I/P (intermediate for 2D6 and poor for 2C19), E for 3A4, I or E for 1A2, the HTR2A genotype is heterozygous (T/C) or homozygous (T/T) and the 5HTTR genotype is heterozygous (l/s) or homozygous (l/l);
  (vi) bupropion, mirtazapine, sertraline, amitriptyline, nortriptyline, venlafaxine and paroxetine if the patient's metabolic phenotype is I/P for 2D6 and 2C19, E for 3A4, P for 1A2, the HTR2A genotype is heterozygous (T/C) or homozygous (T/T) and the 5HTTR genotype is heterozygous (l/s) or homozygous (l/l);
  (vii) bupropion, mirtazapine, fluvoxamine, sertraline, amitriptyline, nortriptyline, and paroxetine if the patient's metabolic phenotype is I/P for 2D6 and 2C19, I or P for 3A4, I or E for 1A2, the HTR2A genotype is heterozygous (T/C) or homozygous (T/T) and the 5HTTR genotype is heterozygous (l/s) or homozygous (l/l);
  (viii) bupropion, mirtazapine, fluvoxamine, sertraline, amitriptyline, nortriptyline, and venlafaxine if the patient's metabolic phenotype is I/P for 2D6 and 2C19, E for 3A4, I or E for 1A2, the HTR2A genotype is homozygous (C/C) and the 5HTTR genotype is heterozygous (l/s) or homozygous (l/l);
  (ix) bupropion, mirtazapine, sertraline, amitriptyline, nortriptyline and paroxetine if the patient's metabolic phenotype is I/P for 2D6 and 2C19, I or P for 3A4, P for 1A2, the HTR2A genotype is heterozygous (T/C) or homozygous (T/T) and the 5HTTR genotype is heterozygous (l/s) or homozygous (l/l);
  (x) bupropion, mirtazapine, sertraline, amitriptyline, nortriptyline, and venlafaxine if the patient's metabolic phenotype is I/P for 2D6 and 2C19, E for 3A4, P for 1A2, the HTR2A genotype is homozygous (C/C) and the 5HTTR genotype is heterozygous (l/s) or homozygous (l/l);
  (xi) bupropion, mirtazapine, fluvoxamine, sertraline, amitriptyline and nortriptyline if the patient's metabolic phenotype is I/P for 2D6 and 2C19, I or P for 3A4, I or E for 1A2, the HTR2A genotype is homozygous (C/C) and the 5HTTR genotype is heterozygous (l/s) or homozygous (l/l);
  (xii) bupropion, mirtazapine, sertraline, amitriptyline and nortriptyline if the patient's metabolic phenotype is I/P for 2D6 and 2C19, I or P for 3A4, P for 1A2, the HTR2A genotype is homozygous (C/C) and the 5HTTR genotype is heterozygous (l/s) or homozygous (l/l);
  (xiii) bupropion, mirtazapine, fluvoxamine, sertraline, amitriptyline, nortriptyline and venlafaxine if the patient's metabolic phenotype is I/P for 2D6 and 2C19, E for 3A4, E for 1A2, the HTR2A genotype is heterozygous (T/C) or homozygous (T/T or C/C) and the 5HTTR genotype is homozygous (s/s);
  (xiv) bupropion, mirtazapine, sertraline, amitriptyline, nortriptyline and venlafaxine if the patient's metabolic phenotype is I/P for 2D6 and 2C19, E for 3A4, I or P for 1A2, the HTR2A genotype is heterozygous (T/C) or homozygous (T/T or C/C) and the 5HTTR genotype is homozygous (s/s);
  (xv) bupropion, mirtazapine, fluvoxamine, sertraline, amitriptyline and nortriptyline if the patient's metabolic phenotype is I/P for 2D6 and 2C19, I or P for 3A4, E for 1A2, the HTR2A genotype is heterozygous (T/C) or homozygous (T/T or C/C) and the 5HTTR genotype is homozygous (s/s);
  (xvi) bupropion, mirtazapine, sertraline, amitriptyline and nortriptyline if the patient's metabolic phenotype is I/P for 2D6 and 2C19, I or P for 3A4, I or P for 1A2, the HTR2A genotype is heterozygous (T/C) or homozygous (T/T or C/C) and the 5HTTR genotype is homozygous (s/s);

(xvii) bupropion, mirtazapine, citalopram, escitalopram, fluvoxamine and sertraline if the patient's metabolic phenotype is P/E (poor for 2D6 and extensive for 2C19), E, I or P for 3A4, E or I for 1A2, the HTR2A genotype is heterozygous (T/C) or homozygous (T/T or C/C) and the 5HTTR genotype is heterozygous (l/s) or homozygous (l/l);

(xviii) bupropion, mirtazapine, citalopram, escitalopram and sertraline if the patient's metabolic phenotype is P/E for 2D6 and 2C19, E, I or P for 3A4, P for 1A2, the HTR2A genotype is heterozygous (T/C) or homozygous (T/T or C/C) and the 5HTTR genotype is heterozygous (l/s) or homozygous (l/l);

(xix) bupropion, mirtazapine, citalopram, escitalopram, and fluvoxamine if the patient's metabolic phenotype is P/E for 2D6 and 2C19, E, I or P for 3A4, E for 1A2, the HTR2A genotype is heterozygous (T/C) or homozygous (T/T or C/C) and the 5HTTR genotype is homozygous (s/s);

(xx) bupropion, mirtazapine, citalopram and escitalopram if the patient's metabolic phenotype is P/E for 2D6 and 2C19, E, I or P for 3A4, I or P for 1A2, the HTR2A genotype is heterozygous (T/C) or homozygous (T/T or C/C) and the 5HTTR genotype is homozygous (s/s);

(xxi) bupropion, venlafaxine, amitriptyline, imipramine, mirtazapine, nortriptyline, fluoxetine, paroxetine, sertraline, citalopram, escitalopram and fluvoxamine if the patient's metabolic phenotype is E/P (extensive for 2D6 and poor for 2C19), E or I for 3A4, E for 1A2, the HTR2A genotype is heterozygous (T/C) or homozygous (T/T or C/C) and the 5HTTR genotype is heterozygous (l/s) or homozygous (l/l);

(xxii) bupropion, amitriptyline, imipramine, mirtazapine, nortriptyline, fluoxetine, paroxetine, sertraline, citalopram, escitalopram and fluvoxamine if the patient's metabolic phenotype is E/P for 2D6 and 2C19, P for 3A4, E for 1A2, the HTR2A genotype is heterozygous (T/C) or homozygous (T/T or C/C) and the 5HTTR genotype is heterozygous (l/s) or homozygous (l/l);

(xxiii) bupropion, venlafaxine, amitriptyline, imipramine, mirtazapine, nortriptyline, fluoxetine, paroxetine, sertraline, citalopram and escitalopram if the patient's metabolic phenotype is E/P for 2D6 and 2C19, E or I for 3A4, I or P for 1A2, the HTR2A genotype is heterozygous (T/C) or homozygous (T/T or C/C) and the 5HTTR genotype is heterozygous (l/s) or homozygous (l/l);

(xxiv) bupropion, amitriptyline, imipramine, mirtazapine, nortriptyline, fluoxetine, paroxetine, sertraline, citalopram and escitalopram if the patient's metabolic phenotype is E/P for 2D6 and 2C19, P for 3A4, I or P for 1A2, the HTR2A genotype is heterozygous (T/C) or homozygous (T/T or C/C) and the 5HTTR genotype is heterozygous (l/s) or homozygous (l/l);

(xxv) bupropion, venlafaxine, amitriptyline, imipramine, mirtazapine, nortriptyline, fluoxetine, paroxetine and sertraline if the patient's metabolic phenotype is E/P for 2D6 and 2C19, E or I for 3A4, E, I or P for 1A2, the HTR2A genotype is heterozygous (T/C) or homozygous (T/T) and the 5HTTR genotype is homozygous (s/s);

(xxvi) bupropion, amitriptyline, imipramine, mirtazapine, nortriptyline, fluoxetine, paroxetine and sertraline if the patient's metabolic phenotype is E/P for 2D6 and 2C19, P for 3A4, E, I or P for 1A2, the HTR2A genotype is heterozygous (T/C) or homozygous (T/T) and the 5HTTR genotype is homozygous (s/s);

(xxvii) bupropion, venlafaxine, amitriptyline, imipramine, mirtazapine, nortriptyline, fluoxetine and sertraline if the patient's metabolic phenotype is E/P for 2D6 and 2C19, E or I for 3A4, E, I or P for 1A2, the HTR2A genotype is homozygous (C/C) and the 5HTTR genotype is homozygous (s/s);

(xxviii) bupropion, amitriptyline, imipramine, mirtazapine, nortriptyline, fluoxetine and sertraline if the patient's metabolic phenotype is E/P for 2D6 and 2C19, P for 3A4, E, I or P for 1A2, the HTR2A genotype is homozygous (C/C) and the 5HTTR genotype is homozygous (s/s);

(xxix) bupropion, mirtazapine, escitalopram, sertraline, amitriptyline, imipramine, nortriptyline, venlafaxine, citalopram, fluvoxamine, fluoxetine and paroxetine if the patient's metabolic phenotype is I/E (intermediate for 2D6 and extensive for 2C19), E for 3A4, E or I for 1A2, the HTR2A genotype is heterozygous (T/C) or homozygous (T/T) and the 5HTTR genotype is heterozygous (l/s) or homozygous (l/l);

(xxx) bupropion, mirtazapine, escitalopram, sertraline, amitriptyline, imipramine, nortriptyline, citalopram, fluvoxamine, fluoxetine and paroxetine if the patient's metabolic phenotype is I/E for 2D6 and 2C19, I or P for 3A4, E or I for 1A2, the HTR2A genotype is heterozygous (T/C) or homozygous (T/T) and the 5HTTR genotype is heterozygous (l/s) or homozygous (l/l);

(xxxi) bupropion, mirtazapine, escitalopram, sertraline, amitriptyline, imipramine, nortriptyline, venlafaxine, citalopram, fluoxetine and paroxetine if the patient's metabolic phenotype is I/E for 2D6 and 2C19, E for 3A4, P for 1A2, the HTR2A genotype is heterozygous (T/C) or homozygous (T/T) and the 5HTTR genotype is heterozygous (l/s) or homozygous (l/l);

(xxxii) bupropion, mirtazapine, escitalopram, sertraline, amitriptyline, imipramine, nortriptyline, venlafaxine, citalopram, fluvoxamine and fluoxetine if the patient's metabolic phenotype is I/E for 2D6 and 2C19, E for 3A4, E or I for 1A2, the HTR2A genotype is homozygous (C/C) and the 5HTTR genotype is heterozygous (l/s) or homozygous (l/l);

(xxxiii) bupropion, mirtazapine, escitalopram, sertraline, amitriptyline, imipramine, nortriptyline, citalopram, fluoxetine and paroxetine, if the patient's metabolic phenotype is I/E for 2D6 and 2C19, I or P for 3A4, P for 1A2, the HTR2A genotype is heterozygous (T/C) or homozygous (T/T) and the 5HTTR genotype is heterozygous (l/s) or homozygous (l/l);

(xxxiv) bupropion, mirtazapine, escitalopram, sertraline, amitriptyline, imipramine, nortriptyline, citalopram, fluvoxamine and fluoxetine if the patient's metabolic phenotype is I/E for 2D6 and 2C19, I or P for 3A4, E or I for 1A2, the HTR2A genotype is homozygous (C/C) and the 5HTTR genotype is heterozygous (l/s) or homozygous (l/l);

(xxxv) bupropion, mirtazapine, escitalopram, sertraline, amitriptyline, imipramine, nortriptyline, venlafaxine, citalopram and fluoxetine if the patient's metabolic phenotype is I/E for 2D6 and 2C19, E for 3A4, P for 1A2, the HTR2A genotype is homozygous (C/C) and the 5HTTR genotype is heterozygous (l/s) or homozygous (l/l);

(xxxvi) bupropion, mirtazapine, escitalopram, sertraline, amitriptyline, imipramine, nortriptyline, citalopram and fluoxetine if the patient's metabolic phenotype is I/E for 2D6 and 2C19, I or P for 3A4, P for 1A2, the HTR2A genotype is homozygous (C/C) and the 5HTTR genotype is heterozygous (l/s) or homozygous (l/l);

(xxxvii) bupropion, mirtazapine, escitalopram, sertraline, amitriptyline, imipramine, nortriptyline, venlafaxine, citalopram and fluoxamine if the patient's metabolic phenotype is I/E for 2D6 and 2C19, E for 3A4, E for 1A2, the HTR2A genotype is heterozygous (T/C) or homozygous (T/T or C/C) and the 5HTTR genotype is homozygous (s/s);

(xxxviii) bupropion, mirtazapine, escitalopram, sertraline, amitriptyline, imipramine, nortriptyline, citalopram and fluoxamine if the patient's metabolic phenotype is I/E for 2D6 and 2C19, I or P for 3A4, E for 1A2, the HTR2A genotype is heterozygous (T/C) or homozygous (T/T or C/C) and the 5HTTR genotype is homozygous (s/s);

(xxxix) bupropion, mirtazapine, escitalopram, sertraline, amitriptyline, imipramine, nortriptyline, venlafaxine and citalopram if the patient's metabolic phenotype is I/E for 2D6 and 2C19, E for 3A4, I or P for 1A2, the HTR2A genotype is heterozygous (T/C) or homozygous (T/T or C/C) and the 5HTTR genotype is homozygous (s/s);

(xl) bupropion, mirtazapine, escitalopram, sertraline, amitriptyline, imipramine, nortriptyline and citalopram if the patient's metabolic phenotype is I/E for 2D6 and 2C19, I or P for 3A4, I or P for 1A2, the HTR2A genotype is heterozygous (T/C) or homozygous (T/T or C/C) and the 5HTTR genotype is homozygous (s/s);

(xli) amitriptyline, bupropion, citalopram, fluvoxamine, imipramine, mirtazapine, nortriptyline, venlafaxine, escitalopram, fluoxetine, paroxetine and sertraline if the patient's metabolic phenotype is E/E (extensive for both 2D6 and 2C19), E or I for 3A4, E or I for 1A2, the HTR2A genotype is heterozygous (T/C) or homozygous (T/T or C/C) and the 5HTTR genotype is heterozygous (l/s) or homozygous (l/l);

(xlii) amitriptyline, bupropion, citalopram, fluvoxamine, imipramine, mirtazapine, nortriptyline, escitalopram, fluoxetine, paroxetine and sertraline if the patient's metabolic phenotype is E/E for 2D6 and 2C19, P for 3A4, E or I for 1A2, the HTR2A genotype is heterozygous (T/C) or homozygous (T/T or C/C) and the 5HTTR genotype is heterozygous (l/s) or homozygous (l/l);

(xliii) amitriptyline, bupropion, citalopram, imipramine, mirtazapine, nortriptyline, venlafaxine, escitalopram, fluoxetine, paroxetine and sertraline if the patient's metabolic phenotype is E/E for 2D6 and 2C19, E or I for 3A4, P for 1A2, the HTR2A genotype is heterozygous (T/C) or homozygous (T/T or C/C) and the 5HTTR genotype is heterozygous (l/s) or homozygous (l/l);

(xliv) amitriptyline, bupropion, citalopram, imipramine, mirtazapine, nortriptyline, escitalopram, fluoxetine, paroxetine and sertraline if the patient's metabolic phenotype is E/E for 2D6 and 2C19, P for 3A4, P for 1A2, the HTR2A genotype is heterozygous (T/C) or homozygous (T/T or C/C) and the 5HTTR genotype is heterozygous (l/s) or homozygous (l/l);

(xlv) amitriptyline, bupropion, citalopram, fluvoxamine, imipramine, mirtazapine, nortriptyline, venlafaxine, escitalopram, fluoxetine, paroxetine and sertraline if the patient's metabolic phenotype is E/E for 2D6 and 2C19, E or I for 3A4, E for 1A2, the HTR2A genotype is heterozygous (T/C) or homozygous (T/T) and the 5HTTR genotype is homozygous (s/s);

(xlvi) amitriptyline, bupropion, citalopram, imipramine, mirtazapine, nortriptyline, venlafaxine, escitalopram, fluoxetine, paroxetine and sertraline if the patient's metabolic phenotype is E/E for 2D6 and 2C19, E or I for 3A4, I or P for 1A2, the HTR2A genotype is heterozygous (T/C) or homozygous (T/T) and the 5HTTR genotype is homozygous (s/s);

(xlvii) amitriptyline, bupropion, citalopram, fluvoxamine, imipramine, mirtazapine, nortriptyline, escitalopram, fluoxetine, paroxetine and sertraline if the patient's metabolic phenotype is E/E for 2D6 and 2C19, P for 3A4, E for 1A2, the HTR2A genotype is heterozygous (T/C) or homozygous (T/T) and the 5HTTR genotype is homozygous (s/s);

(xlviii) amitriptyline, bupropion, citalopram, fluvoxamine, imipramine, mirtazapine, nortriptyline, venlafaxine, escitalopram, fluoxetine and sertraline if the patient's metabolic phenotype is E/E for 2D6 and 2C19, E or I for 3A4, E for 1A2, the HTR2A genotype is homozygous (C/C) and the 5HTTR genotype is homozygous (s/s);

(xlix) amitriptyline, bupropion, citalopram, imipramine, mirtazapine, nortriptyline, escitalopram, fluoxetine, paroxetine and sertraline if the patient's metabolic phenotype is E/E for 2D6 and 2C19, P for 3A4, I or P for 1A2, the HTR2A genotype is heterozygous (T/C) or homozygous (T/T) and the 5HTTR genotype is homozygous (s/s);

(l) amitriptyline, bupropion, citalopram, imipramine, mirtazapine, nortriptyline, venlafaxine, escitalopram, fluoxetine and sertraline if the patient's metabolic phenotype is E/E for 2D6 and 2C19, E or I for 3A4, I or P for 1A2, the HTR2A genotype is homozygous (C/C) and the 5HTTR genotype is homozygous (s/s);

(li) amitriptyline, bupropion, citalopram, fluvoxamine, imipramine, mirtazapine, nortriptyline, escitalopram, fluoxetine and sertraline if the patient's metabolic phenotype is E/E for 2D6 and 2C19, P for 3A4, E for 1A2, the HTR2A genotype is homozygous (C/C) and the 5HTTR genotype is homozygous (s/s); or (lii) amitriptyline, bupropion, citalopram, imipramine, mirtazapine, nortriptyline, escitalopram, fluoxetine and sertraline if the patient's metabolic phenotype is E/E for 2D6 and 2C19, P for 3A4, I or P for 1A2, the HTR2A genotype is homozygous (C/C) and the 5HTTR genotype is homozygous (s/s).

3. The method of claim 1 or 2, wherein the method further comprises receiving, in a computer system, the patients genotype for the panel of genes, said computer system comprising a database, wherein said database comprises a plurality of antidepressant medication profiles.

4. The method of claim 3, wherein one or more of steps 1 and 2 are performed using said computer system and the method further comprises a step of outputting the identity of the antidepressant medication for administering to the patient from the computer system.

5. The method of claim 3, wherein a user enters the patient's genotype in the computer system.

6. The method of claim 4, wherein the patient's genotype is received directly from equipment used in determining the patient's genotype.

7. A non-transitory computer readable medium containing executable instructions that when executed cause a processor to perform operations comprising:
(a) receiving a patient's genotype for a panel of genes, wherein said panel comprises
 (i) a cytochrome P450 CYP2D6 gene consisting of two alleles independently selected from the group consisting of fully functional alleles 2D6*1A, *2, *2N, and *35, partially functional alleles 2D6*10 and *17, and non-functional alleles 2D6*3, *4, *5, *6, *7, *8, and
 (ii) a cytochrome P450 CYP2C19 gene consisting of two alleles independently selected from the group consisting of fully functional alleles 2C19*1A and *1B, and non-functional alleles 2C19*2A, *2B, *3, *4, *5A, *5B, *6, *7 and *8, and
 (iii) a serotonin transporter gene 5HTTR consisting of two alleles independently selected from the short (s) and long (l) forms of the 5HTTR gene;
(b) assigning a metabolic phenotype to the patient based on the genotype of the cytochrome P450 genes in (1), wherein the metabolic phenotype is selected from poor (P), intermediate (I), and extensive (E), and said phenotype is assigned based upon the number of functional alleles for each cytochrome P450 gene as follows: P=no fully functional alleles and either one or no partially functional alleles, I=either one fully functional allele and a non-functional allele or two partially functional alleles, and E=either one fully functional allele and one partially functional allele or two fully functional alleles; and
(c) outputting a list of medications suitable for administering to the patient, said list selected from the group consisting of:
 (i) bupropion, mirtazapine, fluvoxamine and sertraline if the patient's metabolic phenotype is P/P (poor for both 2D6 and 2C19) and the 5HTTR genotype is heterozygous (l/s) or homozygous (l/l);
 (ii) bupropion, mirtazapine and fluvoxamine if the patient's metabolic phenotype is P/P and the 5HTTR genotype is homozygous (s/s);
 (iii) bupropion, mirtazapine, fluvoxamine, sertraline, amitriptyline, nortriptyline, venlafaxine and paroxetine if the patient's metabolic phenotype is I/P (intermediate for 2D6 and poor for 2C19) and the 5HTTR genotype is heterozygous (l/s) or homozygous (l/l);
 (iv) bupropion, mirtazapine, fluvoxamine, sertraline, amitriptyline, nortriptyline and venlafaxine, if the patient's metabolic phenotype is I/P and the 5HTTR genotype is homozygous (s/s);
 (v) bupropion, mirtazapine, citalopram, escitalopram, fluvoxamine and sertraline if the patient's metabolic phenotype is P/E (poor for 2D6 and extensive for 2C19) and the 5HTTR genotype is heterozygous (l/s) or homozygous (l/l);
 (vi) bupropion, mirtazapine, citalopram, escitalopram, and fluvoxamine if the patient's metabolic phenotype is P/E and the 5HTTR genotype is homozygous (s/s);
 (vii) bupropion, venlafaxine, amitriptyline, imipramine, mirtazapine, nortriptyline, fluoxetine, paroxetine, sertraline, citalopram, escitalopram and fluvoxamine if the patient's metabolic phenotype is E/P (extensive for 2D6 and poor for 2C19), and the 5HTTR genotype is heterozygous (l/s) or homozygous (l/l);
 (viii) bupropion, venlafaxine, amitriptyline, imipramine, mirtazapine, nortriptyline, fluoxetine, paroxetine and sertraline if the patient's metabolic phenotype is E/P and the 5HTTR genotype is homozygous (s/s);
 (ix) bupropion, mirtazapine, escitalopram, sertraline, amitriptyline, imipramine, nortriptyline, venlafaxine, citalopram, fluvoxamine, fluoxetine and paroxetine, if the patient's metabolic phenotype is I/E (intermediate for 2D6 and extensive for 2C19) and the 5HTTR genotype is heterozygous (l/s) or homozygous (l/l);
 (x) bupropion, mirtazapine, escitalopram, sertraline, amitriptyline, imipramine, nortriptyline, venlafaxine, citalopram and fluvoxamine, if the patient's metabolic phenotype is I/E and the 5HTTR genotype is homozygous (s/s); and
 (xi) amitriptyline, bupropion, citalopram, fluvoxamine, imipramine, mirtazapine, nortriptyline, venlafaxine, escitalopram, fluoxetine, paroxetine and sertraline if the patient's metabolic phenotype is E/E (extensive for both 2D6 and 2C19) and the 5HTTR genotype is heterozygous (l/s) or homozygous (s/s or l/l).

8. The non-transitory computer readable medium of claim 7, further comprising instructions that when executed cause the processor to execute a step of ranking the medications before outputting the list of medications suitable for administering to the patient.

9. The non-transitory computer readable medium of claim 8, wherein the ranking is adjusted based on receiving a clinical response relating to the patient.

10. The non-transitory computer readable medium of claim 9, wherein the clinical response is by a family member of the patient.

* * * * *

UNITED STATES PATENT AND TRADEMARK OFFICE
CERTIFICATE OF CORRECTION

| | | |
|---|---|---|
| PATENT NO. | : 8,401,801 B2 | Page 1 of 1 |
| APPLICATION NO. | : 10/545931 | |
| DATED | : March 19, 2013 | |
| INVENTOR(S) | : David A. Mrazek et al. | |

It is certified that error appears in the above-identified patent and that said Letters Patent is hereby corrected as shown below:

In the specification:

At column 87, line 22, delete the word "patients" and replace it with the word "patient's".

At column 88, line 58, delete the word "patients" and replace it with the word "patient's".

At column 89, line 17, after the word "gene;", insert the word --and--.

At column 94, line 57, delete the word "patients" and replace it with the word "patient's".

At column 94, line 63, delete the word "a" and replace it with the word "the".

At column 95, line 13, after the word "and", insert the number --*12--.

Signed and Sealed this
Twenty-eighth Day of May, 2013

Teresa Stanek Rea
*Acting Director of the United States Patent and Trademark Office*